United States Patent
Vilhelmsen et al.

(10) Patent No.: US 11,759,502 B2
(45) Date of Patent: *Sep. 19, 2023

(54) COMPOSITIONS OF GLP-1 PEPTIDES AND PREPARATION THEREOF

(71) Applicant: Novo Nordisk A/S, Bagsvaerd (DK)

(72) Inventors: Thomas Vilhelmsen, Strand (DK); Helle Eliasen, Koege (DK); Tue Hansen, Copenhagen (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 17/719,610

(22) Filed: Apr. 13, 2022

(65) Prior Publication Data

US 2022/0331404 A1   Oct. 20, 2022

Related U.S. Application Data

(63) Continuation of application No. 17/157,363, filed on Jan. 25, 2021, which is a continuation of application No. 14/386,589, filed as application No. PCT/EP2013/055362 on Mar. 15, 2013, now Pat. No. 10,933,120.

(60) Provisional application No. 61/748,840, filed on Jan. 4, 2013.

(30) Foreign Application Priority Data

Mar. 22, 2012  (EP) .................................... 12160743
Jan. 31, 2013   (EP) .................................... 13153459

(51) Int. Cl.
*A61K 38/26* (2006.01)
*A61K 9/20* (2006.01)
*A61K 31/20* (2006.01)

(52) U.S. Cl.
CPC ............ *A61K 38/26* (2013.01); *A61K 9/2013* (2013.01); *A61K 9/2077* (2013.01); *A61K 31/20* (2013.01)

(58) Field of Classification Search
None
See application file for complete search history.

(56) References Cited

U.S. PATENT DOCUMENTS

| | | | |
|---|---|---|---|
| 5,545,618 A | 8/1996 | Buckley et al. |
| 5,574,010 A | 11/1996 | McFadden |
| 5,604,203 A | 2/1997 | Balasubramaniam |
| 5,650,386 A | 7/1997 | Leone-Bay et al. |
| 5,773,647 A | 6/1998 | Leone-Bay et al. |
| 5,866,536 A | 2/1999 | Leone-Bay et al. |
| 5,968,899 A | 10/1999 | Sekine et al. |
| 6,046,167 A | 4/2000 | Balasubramaniam |
| 6,071,510 A | 6/2000 | Leone-Bay et al. |
| 6,268,343 B1 | 7/2001 | Knudsen et al. |
| 6,458,924 B2 | 10/2002 | Knudsen et al. |
| 7,049,283 B2 | 5/2006 | Ault et al. |
| 7,235,627 B2 | 6/2007 | Knudson et al. |
| 7,271,149 B2 | 9/2007 | Glaesner et al. |
| 7,417,028 B2 | 8/2008 | Ewing et al. |
| 8,022,035 B2 | 9/2011 | Schwartz et al. |
| 8,039,018 B2 | 10/2011 | Majuru et al. |
| 8,053,429 B2 | 11/2011 | Cumming et al. |
| 8,097,698 B2 | 1/2012 | Knudsen et al. |
| 8,536,122 B2 | 9/2013 | Lau et al. |
| 8,648,041 B2 | 2/2014 | Garibay et al. |
| 8,895,694 B2 | 11/2014 | Spetzler et al. |
| 8,901,073 B2 | 12/2014 | Bloom |
| 9,067,977 B2 | 6/2015 | Spetzler et al. |
| 9,085,637 B2 | 7/2015 | Oestergaard et al. |
| 9,186,392 B2 | 11/2015 | Klein et al. |
| 9,266,940 B2 | 2/2016 | Wieczorek et al. |
| 9,278,123 B2 | 3/2016 | Sauerberg et al. |
| 9,527,900 B2 | 12/2016 | Linderoth et al. |
| 9,993,430 B2 | 6/2018 | Jensen et al. |
| 10,005,827 B2 | 6/2018 | Spetzler et al. |
| 10,086,047 B2 | 10/2018 | Sauerberg et al. |
| 10,246,497 B2 | 4/2019 | Oestergaard et al. |
| 10,278,923 B2 | 5/2019 | Nielsen et al. |
| 10,335,369 B2 | 7/2019 | Vilhelmsen |
| 10,933,120 B2 | 3/2021 | Vilhelmsen et al. |
| 10,960,052 B2 | 3/2021 | Sauerberg et al. |
| 11,033,499 B2 | 6/2021 | Jensen et al. |
| 11,034,746 B2 | 6/2021 | Wieczorek et al. |
| 11,117,947 B2 | 9/2021 | Wieczorek et al. |

(Continued)

FOREIGN PATENT DOCUMENTS

| | | |
|---|---|---|
| CN | 1190893 A | 8/1998 |
| CN | 1867360 A | 11/2006 |

(Continued)

OTHER PUBLICATIONS

King, Simon, "Viewpoints: Novo Nordisk R&D chief predicts an oral revolution for biologies" Nov. 14, 2018, Available from: [http://www.firstwordpharma.com/print/1604592?tsid=17].

Lee, Hye J., "Protein Drug Oral Delivery: The Recent Progress" Archives of Pharmacal Research, 2002, vol. 25, No. 5, pp. 572-584.

Madsen, Kjeld et al., "Structure—Activity and Protraction Relationship of Long-Acting Glucagon-like Peptide-1 Derivatives: Importance of Fatty Acid Lenght, Polarity, and Bulkiness" J. Med. Chem., 2007, vol. 50, pp. 6126-6132.

Morishita, Mariko et al., "Is the oral route possible for peptide and protein drug delivery?" Drug Discovery Today, Oct. 2006, vol. 11, No. 19/20, pp. 905-910.

(Continued)

*Primary Examiner* — Thomas S Heard
(74) *Attorney, Agent, or Firm* — Leon Y. Lum

(57) ABSTRACT

The invention relates to pharmaceutical compositions comprising a first type of granules and a second type of granules, wherein said first type of granules comprises a salt of N-(8-(2-hydroxybenzoyl)amino)caprylic acid and no GLP-1 peptide, and wherein said second type of granules comprises a GLP-1 peptide and no salt of N-(8-(2-hydroxybenzoyl) amino)caprylic acid, as well as the intermediate granules, processes for the preparation of the granules and compositions, and use thereof in medicine.

28 Claims, No Drawings

Specification includes a Sequence Listing.

(56) References Cited

U.S. PATENT DOCUMENTS

| | | |
|---|---|---|
| 2001/0011071 A1 | 8/2001 | Knudsen et al. |
| 2002/0141985 A1 | 10/2002 | Pittner et al. |
| 2005/0009748 A1 | 1/2005 | Dinh et al. |
| 2005/0148497 A1 | 7/2005 | Khan |
| 2005/0176630 A1 | 8/2005 | Cowley et al. |
| 2006/0078622 A1 | 4/2006 | Majuru et al. |
| 2006/0078623 A1 | 4/2006 | Dhoot et al. |
| 2006/0135747 A1 | 6/2006 | Levy et al. |
| 2006/0211610 A1 | 9/2006 | Dong |
| 2006/0286129 A1 | 12/2006 | Sarubbi |
| 2007/0049557 A1 | 3/2007 | Ahmed et al. |
| 2007/0135351 A1 | 6/2007 | Conde-Knape et al. |
| 2007/0197445 A1 | 8/2007 | Balasubramaniam |
| 2007/0203058 A1 | 8/2007 | Lau et al. |
| 2007/0224262 A1 | 9/2007 | Majuru et al. |
| 2008/0076705 A1 | 3/2008 | Kodra et al. |
| 2008/0153779 A1 | 6/2008 | Liao et al. |
| 2008/0194486 A1 | 8/2008 | Bridon et al. |
| 2008/0194676 A1 | 8/2008 | Abbas et al. |
| 2008/0207507 A1 | 8/2008 | Lau et al. |
| 2008/0221038 A1 | 9/2008 | Balasubramaniam |
| 2008/0255250 A1 | 10/2008 | Gomez-Orellana et al. |
| 2008/0269114 A1 | 10/2008 | Schwartz |
| 2009/0088369 A1 | 4/2009 | Steiness |
| 2009/0099074 A1 | 4/2009 | Bridon et al. |
| 2009/0111730 A1 | 4/2009 | Dorwald et al. |
| 2009/0124639 A1 | 5/2009 | Oyewumi et al. |
| 2009/0143330 A1 | 6/2009 | Levchik et al. |
| 2009/0156478 A1 | 6/2009 | Lau et al. |
| 2009/0186811 A1 | 7/2009 | Schwartz |
| 2009/0215682 A1 | 8/2009 | Moore et al. |
| 2010/0016229 A1 | 1/2010 | Sarubbi |
| 2010/0069307 A1 | 3/2010 | Danho et al. |
| 2010/0069410 A1 | 3/2010 | Majuru et al. |
| 2010/0151009 A1 | 6/2010 | Levchik |
| 2010/0210470 A1 | 8/2010 | Citerone et al. |
| 2010/0210526 A1 | 8/2010 | Joshi |
| 2010/0239658 A1 | 9/2010 | Majuru et al. |
| 2010/0292133 A1 | 11/2010 | Spetzler et al. |
| 2010/0317057 A1 | 12/2010 | Lau et al. |
| 2010/0331245 A1 | 12/2010 | Dong |
| 2011/0142800 A1 | 6/2011 | Kidron et al. |
| 2011/0166321 A1 | 7/2011 | Garibay et al. |
| 2011/0218148 A1 | 9/2011 | Azria et al. |
| 2011/0275559 A1 | 11/2011 | Ostergaard et al. |
| 2012/0040893 A1 | 2/2012 | Cowley et al. |
| 2013/0040877 A1 | 2/2013 | Kofoed et al. |
| 2013/0053311 A1 | 2/2013 | Kalthoff et al. |
| 2013/0096055 A1 | 4/2013 | Kofoed et al. |
| 2013/0240587 A1 | 9/2013 | Buchhalter |
| 2013/0345134 A1 | 12/2013 | Sauerberg et al. |
| 2014/0011732 A1 | 1/2014 | Spetzler et al. |
| 2014/0296131 A1 | 10/2014 | Spetzler et al. |
| 2015/0025003 A1 | 1/2015 | Spetzler et al. |
| 2015/0031606 A1 | 1/2015 | Vilhelmsen |
| 2015/0072926 A1 | 3/2015 | Vilhelmsen et al. |
| 2015/0141336 A1 | 5/2015 | Joergensen et al. |
| 2015/0150811 A1 | 6/2015 | Jensen et al. |
| 2016/0067184 A1 | 3/2016 | Nielsen et al. |
| 2016/0151462 A1 | 6/2016 | Sauerberg et al. |
| 2016/0263197 A1 | 9/2016 | Oestergaard et al. |
| 2016/0289283 A1 | 10/2016 | Oestergaard et al. |
| 2017/0312225 A1 | 11/2017 | Nielsen et al. |
| 2017/0313750 A1 | 11/2017 | Oestergaard et al. |
| 2018/0021272 A1 | 1/2018 | Burshtein et al. |
| 2018/0028622 A1 | 2/2018 | Burshtein et al. |
| 2018/0036234 A1 | 2/2018 | Burshtein et al. |
| 2018/0036382 A1 | 2/2018 | Burshtein et al. |
| 2018/0050096 A1 | 2/2018 | Burshtein et al. |
| 2018/0235888 A1 | 8/2018 | Jensen et al. |
| 2018/0251512 A1 | 9/2018 | Wieczorek et al. |
| 2018/0360918 A1 | 12/2018 | Sauerberg et al. |
| 2019/0216739 A1 | 7/2019 | Nielsen et al. |
| 2019/0314283 A1 | 10/2019 | Vilhelmsen |
| 2020/0000728 A1 | 1/2020 | Pedersen et al. |
| 2020/0079834 A1 | 3/2020 | Wieczorek et al. |
| 2020/0147179 A1 | 5/2020 | Bjerregaard et al. |
| 2021/0162012 A1 | 6/2021 | Vilhelmsen et al. |
| 2021/0177944 A1 | 6/2021 | Sauerberg et al. |
| 2021/0275458 A1 | 9/2021 | Bjerregaard et al. |

FOREIGN PATENT DOCUMENTS

| | | |
|---|---|---|
| CN | 101005857 A | 7/2007 |
| CN | 101010339 A | 8/2007 |
| CN | 101133082 A | 2/2008 |
| CN | 101268099 A | 9/2008 |
| CN | 101463081 A | 6/2009 |
| CN | 102946875 A | 2/2013 |
| EP | 0708179 A2 | 4/1996 |
| EP | 0908515 A2 | 4/1999 |
| EP | 1364967 A2 | 11/2003 |
| EP | 2565202 A1 | 3/2013 |
| EP | 2651398 A1 | 10/2013 |
| JP | 05-506427 | 9/1993 |
| JP | H05-506427 A | 9/1993 |
| JP | 2001-504105 A | 3/2001 |
| JP | 2004131398 A | 4/2004 |
| JP | 2006-520818 A | 9/2006 |
| JP | 2007-536268 A | 12/2007 |
| JP | 2008-509933 A | 4/2008 |
| JP | 2009542711 A | 12/2009 |
| JP | 2010-530962 A | 9/2010 |
| JP | 4585037 B2 | 11/2010 |
| JP | 2011509077 A | 3/2011 |
| JP | 2012-121923 A | 6/2012 |
| JP | 2013543814 A | 12/2013 |
| JP | 2014503526 A | 2/2014 |
| JP | 2015-515459 A | 5/2015 |
| KR | 20060100428 A | 9/2006 |
| KR | 102072202 | 1/2020 |
| NZ | 219575 A | 4/1990 |
| RU | 2158138 C2 | 10/2000 |
| RU | 2226402 C2 | 4/2004 |
| RU | 2275207 C2 | 4/2006 |
| WO | 9111457 A1 | 8/1991 |
| WO | 9614854 A1 | 5/1996 |
| WO | 96/29342 | 9/1996 |
| WO | 9725064 A1 | 7/1997 |
| WO | 9808871 A1 | 3/1998 |
| WO | 9820885 A1 | 5/1998 |
| WO | 9820895 A1 | 5/1998 |
| WO | 99/43705 A1 | 9/1999 |
| WO | 99/43706 A1 | 9/1999 |
| WO | 99/43707 A1 | 9/1999 |
| WO | 99/43708 A1 | 9/1999 |
| WO | 9964060 A1 | 12/1999 |
| WO | 9964394 A1 | 12/1999 |
| WO | 00/07617 A1 | 2/2000 |
| WO | 00/16797 A2 | 3/2000 |
| WO | 00/34331 | 6/2000 |
| WO | 200048589 A1 | 8/2000 |
| WO | 00/69911 | 11/2000 |
| WO | 0066629 A1 | 11/2000 |
| WO | 01/04156 | 1/2001 |
| WO | 0124777 A1 | 4/2001 |
| WO | 200141737 A2 | 6/2001 |
| WO | 02/46227 A2 | 6/2002 |
| WO | 0247712 A2 | 6/2002 |
| WO | 0248192 A2 | 6/2002 |
| WO | 03/002158 A1 | 1/2003 |
| WO | 2003005944 A1 | 1/2003 |
| WO | 03/011892 A2 | 2/2003 |
| WO | 03063838 A1 | 8/2003 |
| WO | 03/072195 A2 | 9/2003 |
| WO | 2004/067548 A2 | 8/2004 |
| WO | 04066966 A2 | 8/2004 |
| WO | 2004093823 A2 | 11/2004 |
| WO | 2004/104018 A2 | 12/2004 |
| WO | 2005/005667 A2 | 1/2005 |
| WO | 2005004900 A1 | 1/2005 |
| WO | 2005/014035 A2 | 2/2005 |
| WO | 2005014049 A2 | 2/2005 |
| WO | 2005/027978 A2 | 3/2005 |

(56) References Cited

FOREIGN PATENT DOCUMENTS

| | | |
|---|---|---|
| WO | 2005/028516 A2 | 3/2005 |
| WO | 2005/058954 A1 | 6/2005 |
| WO | 2005/058958 A2 | 6/2005 |
| WO | 2005049061 A2 | 6/2005 |
| WO | 2005/077072 A2 | 8/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005099672 A1 | 10/2005 |
| WO | 2005107462 A2 | 11/2005 |
| WO | 2005107773 A2 | 11/2005 |
| WO | 2005/117984 A2 | 12/2005 |
| WO | 2005/121090 A1 | 12/2005 |
| WO | 2006/005667 A2 | 1/2006 |
| WO | 2006/017251 A2 | 2/2006 |
| WO | 06020207 A2 | 2/2006 |
| WO | 2006/037810 | 4/2006 |
| WO | 06/049681 A2 | 5/2006 |
| WO | 2006/077035 A1 | 7/2006 |
| WO | 2006/082204 A1 | 8/2006 |
| WO | 2006084164 A2 | 8/2006 |
| WO | 2006/097535 A2 | 9/2006 |
| WO | 2006/097536 A2 | 9/2006 |
| WO | 2006/097538 | 9/2006 |
| WO | 2006/097538 A1 | 9/2006 |
| WO | 2006096515 A2 | 9/2006 |
| WO | 2006097537 A2 | 9/2006 |
| WO | 2006103661 A2 | 10/2006 |
| WO | 2006/127948 A2 | 11/2006 |
| WO | 2006124047 A2 | 11/2006 |
| WO | 2007/009894 A2 | 1/2007 |
| WO | 2007008778 A2 | 1/2007 |
| WO | 2007011958 A2 | 1/2007 |
| WO | 2007024700 A2 | 3/2007 |
| WO | 2007/038943 A1 | 4/2007 |
| WO | 2007/038942 A1 | 4/2007 |
| WO | 2007061434 A2 | 5/2007 |
| WO | 2007/068718 A1 | 6/2007 |
| WO | 07065808 A2 | 6/2007 |
| WO | 2007067964 A2 | 6/2007 |
| WO | 2007093226 A1 | 8/2007 |
| WO | 07109354 A2 | 9/2007 |
| WO | 2007117706 A2 | 10/2007 |
| WO | 2007121318 A2 | 10/2007 |
| WO | 2007/128817 A2 | 11/2007 |
| WO | 2007146234 A2 | 12/2007 |
| WO | 2008/003947 A1 | 1/2008 |
| WO | 2008003050 A2 | 1/2008 |
| WO | 2008020096 A1 | 2/2008 |
| WO | 2008028859 A1 | 3/2008 |
| WO | 2008033888 A2 | 3/2008 |
| WO | 2008039351 A2 | 4/2008 |
| WO | 08/053360 A2 | 5/2008 |
| WO | 2008/087186 A2 | 7/2008 |
| WO | 2008/087190 A2 | 7/2008 |
| WO | 2008109385 A2 | 9/2008 |
| WO | 2008132435 A1 | 11/2008 |
| WO | 2008/154619 A1 | 12/2008 |
| WO | 2009007714 A2 | 1/2009 |
| WO | 2009/030771 A1 | 3/2009 |
| WO | 2009030738 A1 | 3/2009 |
| WO | 2009032749 A2 | 3/2009 |
| WO | 2009033710 A1 | 3/2009 |
| WO | 2009/042922 A2 | 4/2009 |
| WO | 2009/050738 A2 | 4/2009 |
| WO | 09042922 A2 | 4/2009 |
| WO | 2009059188 A1 | 5/2009 |
| WO | 2009/083549 A1 | 7/2009 |
| WO | 2009/138511 A1 | 11/2009 |
| WO | 2010020978 A1 | 2/2010 |
| WO | 2010/029159 A1 | 3/2010 |
| WO | 10031707 A1 | 3/2010 |
| WO | 2010031521 A2 | 3/2010 |
| WO | 2010/043319 A1 | 4/2010 |
| WO | 2010052144 A2 | 5/2010 |
| WO | 2010/092163 A2 | 8/2010 |
| WO | 2010096175 A1 | 8/2010 |
| WO | 2011/029551 A2 | 3/2011 |
| WO | 11033068 A1 | 3/2011 |
| WO | 2011033068 A1 | 3/2011 |
| WO | 11045232 A2 | 4/2011 |
| WO | 2011058165 A1 | 5/2011 |
| WO | 2011084618 A2 | 7/2011 |
| WO | 2011094531 A1 | 8/2011 |
| WO | 2011109787 A1 | 9/2011 |
| WO | 2011116139 A2 | 9/2011 |
| WO | 2011131646 A1 | 10/2011 |
| WO | 2011138421 A1 | 11/2011 |
| WO | 2012080471 A1 | 6/2012 |
| WO | 2012140117 A1 | 10/2012 |
| WO | 2013009545 A1 | 1/2013 |
| WO | 2013139694 A1 | 9/2013 |
| WO | 2013139695 A1 | 9/2013 |
| WO | 2013189988 A1 | 12/2013 |
| WO | 2014005858 A1 | 1/2014 |
| WO | 2014177683 A1 | 11/2014 |
| WO | 2014178018 A1 | 11/2014 |
| WO | 2015071355 A1 | 5/2015 |
| WO | 2016128970 A1 | 8/2016 |
| WO | 2016128971 A1 | 8/2016 |
| WO | 2016128972 A1 | 8/2016 |
| WO | 2016128973 A1 | 8/2016 |
| WO | 2016128974 A1 | 8/2016 |
| WO | 2016198682 A1 | 12/2016 |
| WO | 2017060500 A1 | 4/2017 |

OTHER PUBLICATIONS

Novo Nordisk Company announcement No. 14/2015, Novo Nordisk announces positive results for phase 2 trial with oral semaglutide in people with type 2 diabetes, www.novonordisk.com CVR No. 24256790, dated Feb. 20, 2015, p. 1-2.

Novo Nordisk Company announcement No. 52/2015, Novo Nordisk to initiate phase 3a development of oral semaglutide, a once-daily oral GLP-1 analogue, www.novonordisk.com CVR No. 24256790, dated Aug. 26, 2015, p. 1-2.

Novo Nordisk Company announcement No. 17/2018, Novo Nordisk successfully completes the first phase 3a trial, Pioneer 1, with oral semaglutide, www.novonordisk.com CVR No. 24256790, dated Feb. 22, 2018, p. 1-3.

Novo Nordisk Company announcement No. 47/2018, Oral semaglutide shows superior improvement in HbA1C vs empagliflozin in the Pioneer 2 trial, www.novonordisk.com CVR No. 24256790, dated May 29, 2018, p. 1-3.

Novo Nordisk Company announcement No. 51/2018, Oral semaglutide shows statiistically significantly greater reductions in HbA1c and weight compared to Victoza® and sitagliptin in the Pioneer 4 and 7 trials, www.novonordisk.com CVR No. 24256790, dated Jun. 20, 2018, p. 1-4.

Novo Nordisk Company announcement No. 53/2018, Oral semaglutide shows superior reductions in HbA1c and weight compared to sitagliptin in the long-term safety and efficacy trial, Pioneer 3, www.novonordisk.com CVR No. 24256790, dated Jun. 28, 2018, p. 1-3.

Novo Nordisk Company announcement No. 66/2018, Oral semaglutide provides superior HbA1c and weight reductions versus placebo in people with type 2 diabetes and renal impairment in the Pioneer 5 trial, www.novonordisk.com CVR No. 24256790, dated Aug. 20, 2018, p. 1-3.

Novo Nordisk Company announcement No. 74/2018, Oral semaglutide demonstrates greater reductions in HbA1c and body weight and comparable number of adverse events vs dulaglutide in Japanese people with type 2 diabetes, www.novonordisk.com CVR No. 24256790, dated Sep. 20, 2018, p. 1-3.

Novo Nordisk Company announcement No. 81/2018, Oral semaglutide demonstrates statistically significant reductions in HbA1c and body weight in people with long duration of type 2 diabetes treated with insulin, www.novonordisk.com CVR No. 24256790, dated Oct. 26, 2018, p. 1-3.

(56) References Cited

OTHER PUBLICATIONS

Novo Nordisk Company announcement No. 89/2018, Oral semaglutide demonstrates greater reductions in both HbA1c and body weight compared to Victoza® in Japanese people with type 2 diabetes, www.novonordisk.com CVR No. 24256790, dated Nov. 22, 2018, p. 1-2.
Novo Nordisk Company announcement No. 90/2018, Oral semaglutide demonstrates a favourable cardiovascular safety profile and a significant reduction in cardiovascular death and all-casue mortality in people with type 2 diabetes in the Pioneer 6 trial, www.novonordisk.com CVR No. 24256790, dated Nov. 23, 2018, p. 1-3.
Owens, D.R. et al., "Alternative routes of insulin delivery" Diabetic Medicine, 2003, vol. 20, pp. 886-898.
Thepharmaletter, "'8-10 years ahead' of field in oral delivery, senior execs say Novo is becoming a GLP-1 company" May 16, 2018, [cited Jan. 24, 2019] Available from: [https://www.thepharmaletter.com/article/8-10-years-ahead-of-field-in-oral-delivery-senior-execs-say-novo-nordisk-is-becoming-a-glp-1-company].
Watson, Estelle et al., "Population Pharmacokinetics of Liraglutide, a Once-Daily Human Glucagon-Like Peptide-1 Analog, in Healthy Volunteers and Subjects With Type 2 Diabetes, and Comparison to Twice-Daily Exenatide" J. Clin Pharmacology, 2010, vol. 50, pp. 886-894.
Antony J Hickey et al., Pharmaceutical Process Engineering (Second edition) (2010) p. 155-168.
Bruce J. Aungst, "Absorption enhancers: applications and advances," The MPS Journal, 2011, vol. 14, No. 1, pp. 10-18.
Diabetes Close Up, Baby Steps, Mar./Apr. 2011, No. 106, pp. 1-50.
Dilip M. Parikh, Handbook of Pharmaceutical Granulation Technology (Second edition) (2005), Process-related variables, pp. 7-19 and 311-331.
EP Application 12160743, filed Mar. 22, 2012.
EP Application 13153459, filed Jan. 31, 2013.
Full European prosecution file of EP 2 827 885 BI. Published Jan. 28, 2015, Available at the EPO Register, https://register.epo.org/application?number=EP13709231&Ing=en&tab=doclist, accessed May 31, 2019.
Handbook of Pharmaceutical Granulation Technology, Drugs and pharmaceutical sciences, Second Edition, 2005, vol. 154, Introduction, pp. 1-6.
Post-published details of trial NCT01037582. First posted Dec. 23, 2009 https://clinicaltrials.gov/ct2/show/NCT01037582, accessed May 31, 2019.
Published details of trial NCT01037582 First Version Dec. 21, 2009 https://clinicaltrials.gov/ct2/history/NCT01037582?A=1&B=1&C=merged#StudyPageTop, accessed May 31, 2019.
R. F. Witkamp, "Current and Future Drug Targets in Weight Management," Pharm Res, 2011, vol. 28, pp. 1792-1818.
Salem et al., "Approaches to the pharmacological treatment of obesity," Expert Rev Clin Pharmacol, 2010, vol. 3, No. 1, pp. 73-88.
Barrera-Medrano et al., The Handbook of Powder Technology "Granulation", Chp. 25 granule structure, vol. 11, 2007, p. 1189-1212.
U.S. Appl. No. 61/748,840, filed Jan. 4, 2013.
Table summarizing the components of the tablet compositions B to F, described in EP Patent No. 2827885, issued Aug. 15, 2018.
Schematic drawing of tablets E and F described in EP Patent No. 2827885, issued Aug. 15, 2018.
Melanie Davies et al., "Effect of Oral Semaglutide Compared With Placebo and Subcutaneous Semaglutide on Glycemic Control in Patients With Type 2 Diabetes: A Randomized Clinical Trial," JAMA the Journal of the American Medical Association, 2017, vol. 318, No. 15, p. 1460.
Steinert et al., "Oral Administration of Glucagon-Like Peptide 1 or Peptide YY 3-36 Affects Food Intake in Healthy Male Subjects," Am J Clin Nutr, Oct. 2010, vol. 92, No. 4, pp. 810-817.
Full European prosecution file of EP 2 827 885 BI. Available at the EPO Register, https://register.epo.org/application?number=EP13709231&lng=en&tab=doclist, accessed May 31, 2019.

Post-published details of trial NCT01037582 https://clinicaltrials.gov/ct2/show/NCT01037582, accessed May 31, 2019.
Published details of trial NCT01037582 (Dec. 2009) https://clinicaltrials.gov/ct2/history/NCT01037582?A=1&B=1&C=merged#StudyPageTop, accessed May 31, 2019.
Steinert et al., Oral administration of glucagon-like peptide 1 or peptide 3-36 affect food intake in healthy male subjects, "American Society for Nutrition", Am J Clin Nutr, 2010, vol. 92, pp. 810-817.
Nauck et al., 2012, Abstracts of the 48th European Association for the Study of Diabetes Annual Meeting of the EASD, Oct. 1-5, 2012, Berlin, Germany, Diabetologia, 2012, vol. 55, Suppl, S7.
Fonseca et al., "Efficacy and Safety of the Once-Daily GLP-1 Receptor Agonist Lixisenatide in Monotherapy," Diabetes Care, Jun. 2012, vol. 35, pp. 1225-1231.
Study NCT02014259, version 1, published Dec. 18, 2013, accessed Jun. 5, 2019.
"Drug Absorption, Distribution and Elimination; Pharmacokinetics" http://www.columbia.edu/itc/gsas/g9600/2004/GrazianoReadings/Drugabs.pdf, available since at least Apr. 24, 2006, accessed on Jun. 3, 2019.
Standards of Medical Care in Diabetes—2010, "Diabetes Care", vol. 33, supplement 1, Jan. 2010, pp. S11-S61, care.diabetesjournals.org.
Andrew D. Morris, MD, "Addressing dosing frequency in diabetes: a simple approach to improving adherence to therapy and clinical outcomes," The Diabetes Educator, 2003, vol. 29, No. 3, pp. 440-453.
B.J. Aungst, "Absorption Enhancers: Applications and Advances," The AAPS Journal, 2012, vol. 14, No. 1, pp. 10-18.
ClinicalTrials.gov archive: History of Changes for Study NCT01686945, trackchange of version of Apr. 15, 2013 (published Apr. 16, 2013) as compared to version of Sep. 13, 2012 (published Sep. 18, 2012).
ClinicalTrials.gov archive: History of Changes for Study NCT01923181 (NN9924-3790), Jan. 31, 2018, 14 Pages.
Clinicaltrials.gov, NCT01686945, page as viewed in Apr. 2013, https://clinicaltrials.gov/ct2/history/NCT01686945?A=5&B=5&C=merged#StudyPageTop.
Coskun et al., "LY3298176, a novel dual GIP and GLP-1 receptor agonist for the treatment of type 2 diabetes mellitus: From discovery to clinical proof of concept," Molecular Metabolism, 2018, vol. 18, pp. 3-14.
David J. Edmonds et al., "Oral GLP-1 Modulators for the Treatment of Diabetes". Annual Reports in Medicinal Chemistry, 2013, 1st edition, vol. 48, Chapter 9, pp. 119-130.
DJ. Birkett, "Pharmacokinetics made easy 11 Designing dose regimens," Australian Prescriber, 1996, vol. 19, No. 3, pp. 76-88.
E. Mutschler et al., Mutschler Arzneimittelwirkungen, Lehrbuch der Pharmakologie und Toxikologie, 8th edition 2001, pp. 48-51.
Emisphere Annual Report and Proxy 2013, publicly available at the latest on Apr. 17, 2014, 127 pages.
EU Clinical Trials Register Summary EudraCT No. 2012-004994-16 (NN9924-3790), published Jul. 30, 2013, accessed Jun. 7, 2019.
EU Leaflet of Linagliptin, 1st authorization in EU: Aug. 24, 2011 (p. 2, 3 & 13).
EU Leaflet of Linagliptin-Metformin, 1st authorization in EU:Jul. 20, 2012 (p. 2, 3 & 21).
EU Leaflet of Metformin, 1st authorization in EU: Jul. 31, 2001 (p. 1, 2 & 11).
EU Leaflet of Saxagliptin, 1st authorization in EU: Oct. 1, 2009 (p. 1 & 18).
EU Leaflet of Sitagliptin, 1st authorization in EU: Mar. 21, 2007 (p. 2, 3 & 16).
EU Leaflet of Sitagliptin-Metformin, 1st authorization in EU: Jul. 16, 2008 (p. 2, 3 & 20).
EU Leaflet of Vildagliptin, 1st authorization in EU: Sep. 26, 2007(p. 2, 3 & 18).
EU Leaflet of Vildagliptin-Metformin, 1st authorization in EU: Nov. 14, 2007 (p. 2, 3 & 21).
European Patent Application 13166205, filed May 2, 2013.
Geiser et al., "Clinical Pharmacokinetics of Dulaglutide in Patients with Type 2 Diabetes: Analyses of Data from Clinical Trials". Clinical Pharmacokinetics, 2016, vol. 55, pp. 625-634.

(56) References Cited

OTHER PUBLICATIONS

Granhall et al, Safety and Pharmacokinetics of Single and Multiple Ascending Doses of the Novel Oral Human GLP-1 Analogue, Oral Semaglutide, in Healthy Subjects and Subjects with Type 2 Diabetes, Clinical Pharmacokinetics, Dec. 2018.
Leon Shargel, Applied Biopharmaceutics and Pharmacokinetics, 6th edition, 2012, Chapter 8, Multiple-Dosage Regimens, pp. 153-175.
Linda Felton, Remington, Essentials of Pharmaceutics, 2012, Chapter 37, pp. 708-709 and 712-713.
M. Gonzalez Brao, "48th Annual Meeting of the European Association for the Study of Diabetes (EASD)," Drugs of the Future, 2012, vol. 37, No. 12, pp. 871-878.
Malcolm Rowland et al., "Clinical Pharmacokinetics and Pharmacodynamics : Concepts and Applications," Chapter 11—Multiple-Dose Regimens (pp. 293-329); 4th ed.; Philadelphia: Wolters Kluwer Health/Lippincott William & Wilkins, 2011.
Product details regarding "David J. Edmonds et al., Oral GLP-1 Modulators for the Treatment of Diabetes". Annual Reports in Medicinal Chemistry (2013), 1st edition, vol. 48, chapter 9, pp. 119-130, from amazon.com, accessed on May 3, 2019.
Prosecution file of EP2991671B1, available at the EPO Register, the pdf is not attached. https://register.epo.org/application?number=EP14721834&lng=en&tab=doclist, accessed Jun. 14, 2019.
Quianzon et al., "Lixisenatide—Once daily glucagon-like peptide-1 receptor agonist in the management of type 2 diabetes," 2011, US Endocrinology, Diabetes Management, vol. 7, No. 2, pp. 104-109.
Rosenstock et al., "Potential of albiglutide, a long-acting GLP-1 receptor agonist, in type 2 diabetes: a randomized controlled trial exploring weekly, biweekly, and monthly dosing". Diabetes Care, 2009, vol. 32, No. 10, pp. 1880-1886.
S. Dhillon et al., "Basic Pharmacokinetics," Clinical Pharmacokinetics, 2006, Pharmaceutical Press, London; Chapter 1, pp. 1-44.
Sarfaraz K. Niazi, Handbook of Bioequivalence Testing, 2007, p. 13-15.
Schematic overview of sequences and plasma half-life in humans of "GLP-1 peptides" cited as E4 in Sanofi Opposition in EP2991671, dated May 22, 2019, 1 Page.
Sisson, "Liraglutide: clinical pharmacology and considerations for therapy," Pharmacotherapy, 2011, vol. 31, pp. 896-911.
Study NCT01686945, version 1, published Sep. 18, 2012, accessed Jun. 6, 2019.
Study NCT01866748, version 1, published May 31, 2013, accessed Jun. 6, 2019.
Study NCT01923181, version 1, published Aug. 15, 2013, accessed Jun. 5, 2019.
Submission of Novo Nordisk dated Feb. 15, 2019 in response to oppositions against EP2651398B1.
Chae S Y et al., Journal Title: Journal of the Controlled Release,Title: The Fatty Acid Conjugated Exendin-4 Analogs for Type 2 Antidiabetic Therapeutics ,Year: 2010,vol. 144,pp. 10-16.
EP09179390.1 Priority Application Filed on Dec. 16, 2009 by Novo Nordisk. 8067.000-EP, Double-Acylated GLP-1 Derivatives, 100 pages.
EP10190515.6 Priority Application Filed on Nov. 9, 2010 by Novo Nordisk. 8237.000-EP, Double-Acylated GLP-1 Derivatives, 162 pages.
Dolensky et al., "New Building Blocks for Fluorinated Imidazole," Jorunal of Organic Chemistry, vol. 66(13), pp. 4687-4691 (2001).
Knudsen et al., "Potent Derivatives of Glucagon-Like Peptide-1 With Pharmacokinetic Properties Suitable for Once Daily Administration," Journal of Medicinal Chemistry, 2000, vol. 43(9), pp. 1664-1669.
Dumelin et al.., "A Portable Albumin Binder From a DNA-Encoded Chemical Library", Angewandte Chemie (International Edition in English), vol. 47(17), pp. 3196-3201 (2008).
Rawlay SS et al. Journal of Organic Chemistry. "Oxidation of Primary, Secondary, and Tertiary Amines With Neutral Permanganate. A Simple Method for Degrading Amines to Aldehydes and Ketones." 1967. vol. 32(10). pp. 3129-3131.
Travis B R et al. Organic Letters. "Facile Oxidation of Aldehydes to Acids and Esters With Oxone." 2003. vol. 5(7). pp. 1031-1034.
Murage E N et al. Bioorganic & Medicinal Chemistry. "Search for ¿-Helical Propensity in the Receptor-Bound Conformation of Glucagon-Like Peptide-1." 2008. vol. 16. pp. 10106-10112.
Guohu et al "Progress of Pharmaceutical Studies on Diabetes" Practical Pharmacy and Clinic, 2007, vol. 10, No. 1, pp. 56-57.
Zheng, "Formulation and Analytical Development for Low-Dose Oral Drug Products," John Wiley & Sons, Inc., 2009, p. 194.
"International Nonproprietary Names for Pharmaceutical Substances (INN)," WHO Drug Information, 2009, vol. 23, No. 2, p. 129.
Rowe et al.,"Sodium Lauryl Sulfate," Handbook of Pharmaceutical Excipients, 6th Edition, 2009, pp. 651-653.
Ajaz S. Hussain, "A Collaborative Search for Efficient Methods of Ensuring Unchanged Product Quality and Performance During Scale-Up of Immediate-Release Solid Oral Dosage Forms," Pharmaceutical Process Scale-Up, 2002, 1st Edition, Chapter 11, pp. 325-352.
Bai et al., Excipient Development for Pharmaceutical, Biotechnology, and Drug Delivery Systems, 2006, Chapter 12, pp. 181-185.
C. M. Keck et al., "Moderne Pharmazeutische Technologie—Lehbuch fur Studierende," 1. Auflage (2009), Kapitel 1.2 H. J. Ji.inginger, "Delivery Systeme fur die perorale Applikation van Peptiden," pp. 1-14.
European Application No. 12172739.0, filed Jun. 20, 2012.
File History of European Patent 2827845, filed Mar. 15, 2013.
File History of U.S. Appl. No. 61/662,456, filed Jun. 21, 2012.
Rowe et al., "Magnesium Stearate" and "Sodium Lauryl Sulfate", Handbook of Pharmaceutical Excipients, 6th Edition, 2009, pp. 404-407 and 651-653.
History of changes for clinical trial NCT01037582, from Mar. 17, 2011, https://clinicaltrials.gov/ct2/history/NCT01037582?A=5&C=merged#StudyPageTop.
Kikuta et al., "Effect of Mixing Time on the Lubricating Properties of Magnesium Stearate and the Final Characteristics of the Compressed Tablets," Drug Development and Industrial Pharmacy, 1994, vol. 20, No. 3, pp. 343-355.
Kusher IV et al., "Scale-up model describing the impact of lubrication on tablet tensile strength," International Journal of Pharmaceutics, 2010, vol. 399, Nos. 1-2, pp. 19-30.
Lieberman et al., Pharmaceutical Dosage Forms: Tablets, 2nd Edition, 1989, Chapter 5, pp. 247-284.
Parikh, Handbook of Pharmaceutical Granulation Technology, 3rd Edition, 2010, Informa Healthcare, pp. 2-3.
Remington, The Science and Practice of Pharmacy, 21st Edition, 2005, Lippincott, Williams & Wilkins, pp. 677, 892-893, 896, and 1040.
Sakr et al., "Oral Solid Dosage Forms," Remington, Essentials of Pharmaceutics, 1st Edition, Chapter 30, 2012, pp. 581-610.
Valtrex 500mg Tablets—Summary of Product Characteristics (SmPC), Sep. 26, 2019, pp. 1-10.
Teng et al., "Systematical approach of formulation and process development using roller compaction," European Journal of Pharmaceutics and Biopharmaceutics, 2009, vol. 73, pp. 219-229.
Parikh, "Drugs and the Pharmaceutical Sciences", Handbook of Pharmaceutical Granulation Technology, 2010, Third Edition, vol. 198, Chapter 2 Theory of Granulation: An Engineering Perspective, Chapter 8 Roller Compaction Technology and Chapter 9 Wes Granulation in Low- and high-Shear Mixers.
Uros Markoja, Semaglutide—Experiment report for opposition against EP2827845B1, dated Sep. 24, 2019, pp. 1-6.
Valtrex prescribing information (valacyclovir hydrochloride caplets), GlaxoSmithKline, Oct. 2007, pp. 1-20.
Venables et al., "Powder Mixing," Drug Development and Industrial Pharmacy, 2001, vol. 27, No. 7, pp. 599-612.
Tyagi et al., "Oral peptide delivery: Translational challenges due to physiological effects," J. Controlled Release, 2018, vol. 287, pp. 167-176.
Dahlgren et al., "Intestinal absorption-modifying excipients: A current update on preclinical in vivo evaluations," European J. of Pharm. and Biopharmaceutics, 2019, vol. 142, pp. 411-420.

(56) References Cited

OTHER PUBLICATIONS

Figures presenting plasma concentration, described in EU Patent No. 2991671, issued Aug. 15, 2018.
FDA News Release, "FDA approved first oral GLP-1 treatment for type 2 diabetes," Sep. 20, 2019.
Carly Helfand, "Novo Nordisk wins FDA green light for "holy grail" diabetes drug Rybelsus," Fierce Pharma, Sep. 20, 2019, https://www.fiercepharma.com/pharma/novo-nordisk-wins-fda-green-light-for-holy-grail-oral-semaglutide, accessed Oct. 4, 2019.
Runge et al., "Crystal Structure of the Ligand-Bound Glucagon-Like Peptide-1 Receptor Extracellular Domain," J Biol Chem 2008, vol. 283, No. 17, pp. 11340-11347.
Adelhorst, K et al Journal of Biological Chemistry Structure Activity Studies of GLP-1 1994 269 9 6275-6278.
Knudsen, L.B. Journal of Medicinal Chemistry Glucagon-Like Peptide-1: The Basis of a New Class of Treatment for Type 2 Diabetes 2004 47 17 4128-4134.
Leger et al., "Identification of CJC-1131-Albumin Bioconjugate as a Stable and Bioactive GLP-1 (7-36) Analog," Bioorganic and Medicinal Chemistry Letters, vol. 14, pp. 4395-4398 (2004).
Pan et al., Design of a Long Acting Peptide Functioning as both a Glucagon-like Peptide-1 Receptor Agonist and a Glucagon Receptor Antagnist, "The Journal of Biological Chemistry", May 2006, vol. 281, No. 18, pp. 12506-12515.
The Medical Dictionary Online. http://cancerweb.ncl.ac.uklomd/about.html. 2005.
Nauck, M A. Regulatory Peptides. "Glucagon-Like Peptide 1 and its Derivatives in the Treatment od Diabetes." 2005. vol. 128(2). pp. 135-148.
David M. Irwin, Trout and chicken Proglucagon: Alternative Splicing Generates mRNA Transcripts Encoding Glucagon-Like Peptide 2, Molecular Endocrinology, 1995, vol. 9 No. 3, 267-277.
Overview of claim 1 of the main and auxiliary requests, European Application No. EP2651398, filed May 14, 2013.
GenScript, "Peptide YY (PYY) (3-36), human," https://www.genscript.com/peptide/RP10354-Peptide_YY_PYY_3_36_human.html, accessed Jan. 27, 2020.
Banakar et al., Critical Considerations in Pharmaceutical Bioequivalence Testing, Journal of Pharmacy of University of Marmara, 1995, vol. 11 Nos. 1-2, pp. 55-80.
Emisphere Technologies, Inc., Form 10-K, 2013 Annual Report, Published Mar. 31, 2014.
American Veterinary Medical Association, "The Veterinarian-Client-Patient Relationship (VCPR)," https://www.avma.org/policies/veterinarian-client-patient-relationship, accessed Mar. 11, 2020.
National Institute of Diabetes and Digestive and Kidney Diseases, "Prescription Medications to Treat Overweight and Obesity," Jul. 2016, 10 pages, retrieved on Apr. 13, 2020, URL: https://www.niddk.nih.gov/health-information/weight-management/prescription-medications-treat-overweight-obesity.
W.K. Sietsema, "The absolute oral bioavailability of selected drugs." Mar. 1989, International Journal of Clinical Pharmacology, Therapy and Toxicology, vol. 27, No. 4, pp. 179-211.
Declaration of Doctor Peter Rue, for EP2827885 dated Jul. 29, 2020.
Declaration of Professor Leon Aarons for EP2827885 dated Jul. 29, 2020.
Shajahan et al., A flexible technology for modified-release drugs: Multiple-unit pellet system (MUPS) May 2009, Journal of Controlled Release, vol. 147, No. 1, pp. 2-16.
Physicians' Desk Reference, 54th Edition, 2000, p. 1291.
Physicians' Desk Reference, 63rd Edition, 2009, p. 1638.
Arbit et al. "Oral heparin: status review". Thrombosis J, May 2006, vol. 4, No. 6, pp. 1-7.
Emisphere Announces License Agreement With Novo Nordisk to Develop Oral Formulation of GLP-1 Receptor Agonists for Diabetes, Jun. 23, 2008 retrieved from https://www.biospace.com/article/releases/emisphere-technologies-inc-announces-license-agreement-with-novo-nordisk-inc-to-develop-oral-formulation-of-glp-1-receptor-agonists-for-diabetes-/, 5 pages, retrieved on Dec. 16, 2020.
European Medicines Agency, Rybelsus EPAR Public Assessment Report, Jan. 30, 2020, pp. 1-152, p. 72.
Notice of Opposition by Galenicum, filed Dec. 9, 2020 in European Patent 3326620.
Notice of Opposition by Hexal Ag, filed Dec. 8, 2020 in European Patent 3326620.
Novo Nordisk starts phase 1 trial with long-acting oral GLP-1 analogue, Jan. 13, 2010, 2 pages retrieved from https://pipelinereview.com/index.php/2010011332046/Small-Molecules/Novo-Nordisk-starts-phase-1-trial-with-long-acting-oral-GLP-1-analogue.html, retrieved on Dec. 16, 2020.
Novo Nordisk, "Novo Nordisk to acquire Emisphere Technologies and obtain ownership of the Eligen® SNAC oral delivery technology", Nov. 6, 2020 retrieved from <https://www.novonordisk.com/content/nncorp/global/en/news-and-media/news-and-ir-materials/news-details.html?id=33374>, 3 pages retrieved on Dec. 16, 2020.
Notice of Opposition by Teva filed Dec. 4, 2020 in European Patent 3326620.
Bryan J. Ennis, "Theory of Granulation: An Engineering Perspective," Handbook of Pharmaceutical Granulation Technology, 2005, pp. 7-78.
Pechenov et al., "Development of an orally delivered GLP-1 receptor agonist through peptide engineering and drug delivery to treat chronic disease," Scientific Reports, Nov. 2021, vol. 11, No. 22521, pp. 1-15.
Wong et al., "Estimation of clinical trial success rates and related parameters," Biostatistics, Jan. 2018, vol. 20, No. 2, pp. 273-286.
Novo Nordisk Reply to Office Action dated Jul. 3, 2008 in EP1863839.
Gomez-Orella, "Strategies to Improve Oral Drug Bioavailability," Expert Opin Drug Deliv, 2005, vol. 2, No. 3: pp. 419-433.
Humphrey, M. J., "The Oral Bioavailability of Peptides and Related Drugs. In Delivery Systems for Peptide Drugs," Davis, S.S., Ilium, L., Tomlinson, E., Eds.; Springer: Boston, MA, 1986; pp. 139-151.
Novo Nordisk's reply to the examination division dated Nov. 18, 2016 in EP Application 13729743.8, 3 pages.
Novo Nordisk's reply to the opposition grounds of WO2012/080471, corresponding to EP2651398, dated Feb. 15, 2019, 40 pages.
Kwan et al., "Factors Affecting Tablet Disintegration," Journal of the American Pharmaceutical Association, Scientific Edition, Apr. 1957, vol. XLVI, No. 4, pp. 236-239.
Viscasillas i Clerch, "Aportacion al diseno de un nuevo excipiente tipo "coprocessed product" para compresion directa," Universitat de Barcelona, 2008, pp. 159-160.
Pharmaceutical Binders and Their Function in Directly Compressed Tablets, Mechanistic Studies on the Effect of Dry Binders on Mechanical Strength, Pore Structure and Disintegration of Tablets, Dissertation for the Degree of Doctor of Philosophy (Faculty of Pharmacy) in Pharmaceutics presented at Uppsala University in 2000 By Sofia Mattsson, pp. 32-34.
Extract of the opposed patent EP2863895, 2 pages, full prosecution file can be found in European Patent register https://register.epo.org/application?number=EP13729743&Ing=en&tab=doclist.
Anne Mari Juppo, "Porosity parameters of lactose, glucose and mannitol tablets obtained by mercury porosimetry," International Journal of Pharmaceutics, 1996, vol. 129, pp. 1-12.
Michael E. Aulton., "Aulton's Pharmaceutics. The design and manufacture of medicines" Churchill Livingstone Elsevier, 2007, Ed. 3rd, Chapter 21, pp. 286-303.
Linda Felton, "Remington Essentials of Pharmaceutics," Pharmaceutical Press, 2012, Chapter 6, pp. 63-80 and Chapter 30, pp. 581-610.
Qiu et al., "Developing Solid Oral Dosage Forms" Pharmaceutical Theory and Practice, Academic Press, 2009, 1st Edition, pp. 175-186.
James Swarbrick, "Encyclopedia of Pharmaceutical Technology. vol. 1," Informa Healthcare USA, Inc., 2007, Ed. 3rd, pp. 164-175 and 988-1000.
EP application No. 12160743.6, filed Mar. 22, 2012.
Betts et al., Chapter 14, "Amino Acid Properties and Consequences of Substitutions," Bioinformatics for Geneticists (2003) ed. By Barnes and Gray, John Wiley & Sons, Ltd., pp. 289-316.

(56) References Cited

OTHER PUBLICATIONS

Kojima S et al. A role for pancreatic polypeptide in feeding and body weight regulation, "Peptides", Year 2007, vol. 28, No. 2, pp. 459-463.
Lin Shu et al. Critical Role of Arcuate Y4 Receptors and the Melanocortin System in Pancreatic Polypeptide-Induced Reduction in Food Intake in Mice, "PLOS One" Year 2009, vol. 4, No. 12, pp. e8488-e8488.
Ito T et al, Effects of peripheral administration of PYY3-36 on feed intake and; plasma acyl-ghrelin levels in pigs, Journal of Endocrinology, Year 2006, vol. 191, pp. 113-119.
Ortiz A. et al, A Novel Long-Acting Selective Neuropeptide Y2 Receptor Polyethylene Glycol-Conjugated Peptide Agonist Reduces Food Intake and Body Weight and Improves Glucose Metabolism in Rodents, The Journal of Pharmacology and Experimental Therapeutics (2007), vol. 323, No. 2, pp. 692-700.
Roger Reidelberger et al., Effects of Glycine-Extended and Serine 13-Phosphorylated Forms of Peptide YY on Food Intake in Rats, Peptides, Year 2011; vol. 32, No. 4, pp. 770-775.
Søren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
van den Hoek A. et al., Chronic PYY3-36 treatment promotes fat oxidation and ameliorates insulin resistance in C57BL6 mice, American Journal of Physiology—Endocrinology and Metabolism, Year 2007, 292, pp. E238-E245.
Adrian et al., Gut, 1978, vol. 19, No. 10, pp. 907-909.
Heizmann et al., Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.
Batterham, R.L. et al., "Gut Hormone PYY3-36 Physiologically Inhibits Food Intake", Nature, 2002, vol. 418, pp. 650-654.
Bowie et al. (Science, 1990, 247:1306-1310).
Burgess et al. (J. Cell Biol. 111:2129-2138, 1990).
Lazar et al. (Mol. Cel. Biol., 8:1247-1252, 1988).
Bork (Genome Research, 2000, 10:398-400).
T.W. Schwartz., "Pancreatic Polypeptide: A Hormone Under Vagal Control", Gastroenterology. 1983, vol. 85, pp. 1411-1425.
Whitcomb. Am. J. Physiol. "Characterization of saturable binding sites for circulating pancreatic polypeptide in rat brain." 1990 vol. 259 G687-G691.
Jorgensen, J. Ch et al. Euro. J. Pharmacol. "Structure-function studies on neuropeptide Y and pancreatic polypeptide—evidence for two PP-fold receptors in vas deferens" 1990 vol. 186: 105-114.
Cooke, D et al. Nature Reviews. "The obesity pipeline: current strategies in the development of anti-obesity drugs" 2006 vol. 5: 919-930.
Kamiji, M.M et al. Current Topics in Medical Chemistry "NPY Y2 and Y4 receptors selective ligands: promising anti-obesity drugs?" 3008 vol. 7: 1734-1742.
Sainsbury, A. et al. Mol Nad Cell Biol "Synergistic Effects of Y2 and Y4 Receptors on Adiposity and Bone Mass Revealed in Double Knockout Mice" vol. 23: 5225-5233.
Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403.
Knudsen et al. J Med Chem. "Potent Derivatives of Glucagon-Like Peptide-1 with Pharmacokinetic Properties Suitable for Once Daily Administration" 2000. vol. 43(9). p. 1664-1669.
Boggiano, M.M. et al, "PYY3-36 as an anti-obesity drug target", Obesity Reviews. 2005 vol. 6: 307-322.
Dodson, Shontelle et al "Muscle Wasting in Cancer Cachexia: Clinical Implications, Diagnosis, and Emerging Treatment Strategies" Annu. Rev. Med. 2011 vol. 62 pp. 265-279.
Muscaritoli, Maurizio et al "Prevention and Treatment of Cancer Cachexia: New Insights into an Old Problem." European Journal of Cancer, 2006 vol. 42 pp. 31-41.

Soeren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.
van den Hoek A. et al., Chronic PYY3-36 treatment promotes fat oxidation and ameliorates insulin resistance in C57BL6 mice, American Journal of Physiology—Endocrinology and Metabolism, Year 2007, vol. 292, No. 1 pp. E238-E245.
Kouki Kitagawa et al: Solution synthesis of human peptide YY(hPYY),Chemical & Pharmaceutical Bulletin,Year Jun. 1, 1990 vol. 38, No. 6, pp. 1731-1734.
Ortiz A. et a IA Novel Long-Acting Selective Neuropeptide Y2 Receptor Polyethylene Glycol-Conjugated Peptide Agonist Reduces Food Intake and Body Weight and Improves Glucose Metabolism in Rodents, The Journal of Pharmacology and Experimental Therapeutics Year 2007, vol. 323 No. 2, pp. 692-700.
Roger Reidelberger et al: "Effects of glycine-extended and serine-phosphorylated forms of peptide YY on food intake in rats", Peptides,Peptides Year 2011,vol. 32, No. 4, pp. 770-775.
Van den Hoek A. et al Chronic PYY3-36 treatment promotes fat oxidation and ameliorates insulin resistance in C57BL6 mice American Journal of Physiological Endocrinology and Metabolism Year 2006,vol. 292, No. 1 pp. E238-E245.
Balasubramaniam et al., "Structure-Activity Studies Including a psi(CH2-NH) Scan of Peptide YY (PYY) Active Site, PYY(22-36), for Interaction with Rat Intestinal PYY Receptors: Development of Analogues with Potent in Vivo Activity in the Intestine," J. Med. Chem., 2000, vol. 43, pp. 3420-3427.
Atherosclerosis, from http://www.merckmanuals.com/professional/cardiovascular-disorders/arteriosclerosis/atherosclerosis, pp. 1-14, accessed Dec. 29, 2015.
Diabetes, from http://www.merckmanuals.com/professional/endocrine-and-metabolic-disorders/ . . . , pp. 1-34, accessed Sep. 2, 2016.
Dyslipidemia, from http://www.merckmanuals.com/professional/endocrine-and-metabolic-disorders/lipid-dis . . . , pp. 1-11, accessed Dec. 29, 2015.
Fatty Liver Disease, from http://www.webmd.com/hepatitis/fatty-liver-disease?page=2&print=true, pp. 1-4, accessed Dec. 29, 2015.
Nabel, "Cardiovascular Disease," New Engl. J. Med., 2003, vol. 349, pp. 60-72.
Neary et al., "Peptide YY: Food for thought," Physiology & Behavior 97: 616-619 (2009).
Nonatheromatous Arteriosclerosis, from http://www.merckmanuals.com/professional/cardiovascular-disorders/arteriosclerosis/non . . . , pp. 1-2, accessed Dec. 29, 2015.
Sam et al., "Selective Ablation of Peptide YY Cells in Adult Mice Reveals Their Role in Beta Cell Survival," Gastroenterology, 143:459-468 (2012).
Vincent et al., "The satiety hormone peptide YY as a regulator of appetite," J Clin Pathol 61 :548-552 (2008).
Zhao Na et al., "PYY and obesity (summary)," Sports and Research Education, 2012, vol. 27, No. 3, pp. 102-107.
Huang Lan et al., "Relationship between Peptide Tyrosine-Tyrosine 3-36 and Ingestion Regulation," Hubei Agriculture Sciences, 2009, vol. 48, No. 10, pp. 2591-2594.
Zhao Biqian et al., "Regulation of PYY on Animal Food Intakes," Feed Industry, 2010, vol. 31, No. 18, pp. 51-55.
Beglinger et al. "Pharmacokinetics and pharmacodynamic effects of oral GLP?1 and PYY3?36: a proof?of?concept study in healthy subjects" Clinical Pharmacology & Therapeutics, Oct. 2008, vol. 84, No. 4, pp. 468-474.
Schmidt et al., "Effects of PYY3-36 and GLP-1 on energy intake, energy expenditure, and appetite in overweight men." American Journal of Physiology—Endocrinology and Metabolism, Apr. 2014, vol. 306, No. 11, pp. E1248-E1256.
Steinert et al.,"Oral administration of glucagon-like peptide 1 or peptide YY 3-36 affects food intake in healthy male subjects." The American journal of clinical nutrition, Oct. 2010, vol. 92, No. 4, p. 810-817.
Cox Gad, Shayne, "Pharmaceutical Manufacturing Handbook Production and Processes," Hoboken, New Jersey: Wiley-Interscience A John Wiley & Sons, Inc., 2008, pp. 235-265 and 881-1222.

(56) References Cited

OTHER PUBLICATIONS

Hancock et al., "The Relative Densities of Pharmaceutical Powders, Blends, Dry Granulations, and Immediate-Release Tablets," Pharmaceutical Technology, Apr. 2003, p. 64-80.
Hoffman et al., "Eligen insulin—a system for the oral delivery of insulin for diabetes," IDrugs, 2008, vol. 11, pp. 433-441.
Lowenthal, Werner, "Disintegration of Tablets" Journal of Pharmaceutical Sciences, Nov. 1972, vol. 61, No. 11, pp. 1695-1711.
Poole, John W., "Effects of Formulation and Dosage Form on Drug Bioavailability" Principles and Perspectives in Drug Bioavailability, Chapter 3, Karger, 1979, pp. 59-89.
Rudnic et al., "Oral Solid Dosage Forms," Chapter 45, Remington—The Science and Practice of Pharmacy, Philadelphia, PA: Lippincott Williams & Wilkins, 2006, Ed. 21st, pp. 889-927.
Tong, W.Q., "Molecular and Physicochemical Properties Impacting Oral Absorption of Drugs" Biopharmaceutics Applications in Drug Development, Chapter 2, Springer, 2008, pp. 26-46.
Study protocol of trial NCT01037582 of Dec. 2009, 7 pages.
Liang Wenquan, "II. Effect of dosage form on drug absorption; V. Basic Requirements for Bioavailability Research", Biopharmaceutics and Pharmacokinetics, Jul. 31, 2003, 2nd Edition, pp. 38-40, 332-335.
Beglinger C et al., Pharmacokinetics and Pharmacodynamic Effects of Oral GLP-1 and PYY3-36: A Proof-of-concept Study in Healthy Subjects, Journal: Clinical Pharmacology & Therapeutics, Nature Publishing Group, Year: 2008. vol. 84, No. 4, pp. 468-474.
Leonard Thomas W et al., Promoting absorption of drugs in humans using medium-chain fatty acid-based solid dosage forms:GIPET™, Journal: Expert Opinion Drug Delivery, Year 2006, vol. 3(5), pp. 685-692.
Maher Sam et al., Overcoming poor permeability: translating permeation enhancers for oral peptide delivery, Journal: Drug Discovery Today: Technologies, Year 2011, vol. 9, No. 2, pp. e113-e119.
Maher Sam et al., Safety and efficacy of sodium caprate in promoting oral drug absorption: from in vitro to the clinic, Journal: Advanced Drug Delivery Reviews, Year 2009, vol. 61, pp. 1427-1449.
Michel Marre et al., GLP-1 receptor agonists today, Journal. Diabetes Research; and Clinical Practice, Year: 2011, vol. 93, No. 3, pp. 317-327.
Walsch Edwin G et al., Oral delivery of macromolecules: rationale underpinning Gastrointestinal Permeation Enhancement Technology (GIPET®), Journal: Therapeutic Delivery, Year: 2011, vol. 2, No. 12, pp. 1595-1610. OTH.
Beglinger C et al., Clinical Pharmacology and Therapeutics,"Pharmacokinetics and Pharmacodynamic Effects of Oral GLP-1 and PYY3-36: A Proof-of-Concept Study in Healthy Subjects"., 2008, vol. 84, No. 4, pp. 468-474.
Steinert RE et al, American Journal of Clinical Nutrition,"Oral Administration of Glucagon-Like Peptide 1 or Peptide YY 3-36 Affects Food Intake in Healthy Male Subjects", 2010, vol. 92, pp. 810-817.
He Xiaorong et al., Mechanistic Study of the Effect of Roller Compaction and Lubricant on Tablet Mechanical Strength, Journal: Journal of Pharmaceutical Sciences,Year: 2007, vol. 96, No. 5, pp. 1342-1355.
Mollan Jr. Matthew J. et al., The effects of lubrication on the compaction and post-compaction properties of directly compressible maltodextrins, Journal: International Journal of Pharmaceutics, Year: 1996, vol. 144, Issue 1, pp. 1-9.
Rowe Raymond C et al., Book: Handbook of Pharmaceutical Excipients, Title: Acesulfame Potassium, Edition—5th, Year: 2006, Complete book.
Steinert R E et al., Orally Administered Glucagon-Like Peptide-1 Affects Glucose Homeostasis Following an Oral Glucose Tolerance Test in Healthy Male Subjects, Journal: Clinical Pharmacology And Therapeutics, Year: 2009, vol. 86, No. 6, pp. 644-650.
von Eggelkraut-Gottanka Stephan G. et al., Roller Compaction and Tabletting of St. John's Wort Plant Dry Extract Using a Gap Width and Force Controlled Roller; Compactor. II. Study of Roller Compaction Variables on Granule and Tablet Properties by a 33 Factorial Design, Journal: Pharmaceutical Development and Technology, Year: 2002, vol. 7, No. 4, pp. 447-455.
Makoto Otsuka, Chemoinformetrical evaluation of granule and tablet properties of pharmaceutical preparations by near-infrared spectroscopy, "Chemometrics and Intelligent Laboratory Systems" Year 2006, vol. 82, No. 1-2, pp. 109-114.
Shah R. B et al. Process Analytical Technology: Chemometric Analysis of Raman and Near Infra-red Spectroscopic Data for Predicting Physical Properties of Extended Release Matrix Tablets, "Journal of Pharmaceutical Sciences" Year 2007, vol. 96, No. 5, pp. 1356-1365.
Aenugu H.P.R et al. Near Infra Red Spectroscopy—An Overview, "International Journal of ChemTech Research" Year 2011, vol. 3, No. 2, pp. 825-836.
Donoso M et al. Prediction of Tablet Hardness and Porosity Using Near-Infrared Diffuse Reflectance Spectroscopy as a Nondestructive Method, "Pharmaceutical Development and Technology" Year 2003, vol. 8, No. 4, pp. 357-366.
Jeckel et al. Importance of particle size knowledge for tablet porosity determination by NIRS, "Tablet Tech Seminar, FMC Biopolymer" Year 2007, retrieved from the Internet: URL:http://www.pharmtech.uni-bonn.de/forschung/arbeitskreis-porf-steffens/download-16, the whole document.
Remington, The Science and Practice of Pharmacy, 22nd Edition, 2012.
Felix Kratz "A Clinical Update of Using Albumin as a Drug Vehicle—A Commentary" Journal of Controlled Release 2014 vol. 190 pp. 331-336.
Rivera et al. Oral Delivery of Heparin in Combination with Sodium N-[8-(2-Hydroxybenzoyl)amino]caprylate: Pharmacological Considerations. Pharmaceutical Research 1997 vol. 14 No. 12 pp. 1830-1834.
Su Young Chae et al. "Preparation, Characterization and Application of Biotinylated and Biotin-PEGylated Glucagon-Like Peptide-1 Analogues for Enhanced Oral Delivery" Bioconjugate Chemistry 2008 vol. 19 No. 1 pp. 334-341.
Emisphere Technologies. "Carriers Enhance Drug Delivery" Manufacturing Chemistry 1999 vol. 70 No. 6 pp. 25-26.
Adam W. G. Alani et al., "Mechanistic Understanding of Oral Drug Absorption Enhancement of Cromolyn Sodium by an Amino Acid Derivative," Pharmaceutical Research, 2008, vol. 25, No. 1, pp. 48-54.
Granulation Handbook, Chapter 4. Compression Granulation Method, May 30, 1975, 1st Edition First Press, p. 173-197.
Design and evaluation of formulation for oral administration, Problem arising from industrialization and process scale-up and corresponding solutions, Feb. 10, 1995, p. 264-279.
Bhansali et al., "Historical Overview of Incretin Based Therapies," Supplement to JAPI, 2010, vol. 58, pp. 10-14.
Valentino et al., "Central and Peripheral Molecular Targets for Antiobesity Pharmacotherapy," Clinical Pharmacology and Therapeutics, 2010, vol. 87, No. 6, pp. 652-662.
Bastin et al., "Salt Selection and Optimisation Procedures for Pharmaceutical New Chemical Entities," Org Proc Res & Devt, 2000, vol. 4, pp. 427-435.
Drug Data Report, 2006, vol. 28, p. 933.
Anonymous, "Eligen@ Technology. Summary and Value Proposition", Emisphere, Feb. 24, 2017, pp. 1-10, URL: https://www.emisphere.com/wp-content/uploads/2017/02/Eligen-Technology-Presentation_2.15-Update.pdf, XP055520567.
Keck et al., Moderne Pharmazeutische Technologie, 2009, pp. 8-14.
Kidron et al., "A Novel Per-Oral Insulin Formulation: Proof of Concept Study in Non-Diabetic Subjects," Diabetic Medicine, 2004, vol. 21, pp. 354-357.
Letter to Sandoz International GmbH regarding English translation of claim of patent JP4585037, dated Aug. 29, 2018.
Mullins, "Statistics for the Quality Control Chemistry Laboratory," 2003, Chapter 1, pp. 10-17.
SNAC, Synchem, http://www.synchem.de/product/snac, accessed Aug. 16, 2018.

(56) References Cited

OTHER PUBLICATIONS

Valentino et al., "Current Trends in Targeting the Hormonal Regulation of Appetite and Energy Balance to Treat Obesity," Expert Rev Endocrinol Metab, 2010, vol. 5, pp. 765-783.
WHO Drag Information, "International Nonproprietary Names for Pharmaceutical Substances," 2009, vol. 23, No. 2, p. 164.
U.S. Appl. No. 61/425,087, filed Dec. 20, 2010.
EP Application No. 10195285.1, filed Dec. 16, 2010.
Wang et al., "Non-peptidic glucose-like peptide-1 receptor agonists: aftermath of serendipitous discovery," Acta Pharmacol. Sinica, 2010, vol. 31, pp. 1026-1030.
Baynes, Kevin C. R., "The evolving world of GLP-1 agonist therapies for type 2 diabetes" Therapeutic Advances in Endocrinology and Metabolism, 2010,,vol. 1, No. 2, pp. 61-67.
Buckley, Stephen T. et al., "Transcellular stomach absorption of a derivatized glucagon-like peptide-1 receptor agonist" Science Translational Medicine, Nov. 14, 2018, vol. 10, pp. 1-14.
Christensen, Mikkel et al., "Once-Weekly GLP-1 Agonists: How Do They Differ from Exenatide and Liraglutide?" Curr Diab Rep, 2010, vol. 10, pp. 124-132.
Davies, Melanie et al., "Effect of Oral Semaglutide Compared with Placebo and Subcutaneous Semaglutide on Glycemic Control in Patients with Type 2 Diabetes" JAMA, 2017, vol. 318, pp. 1460-1470.
Declaration by the Inventor, Flemming S. Nielsen, dated Feb. 11, 2019.
EMEA Assessment Report EMEA/379172/2009 for Victoza (liraglutide), 2009.
Goldberg, Michael et al., "Challenges for the Oral Delivery of Macromolecules" Nature Reviews Drug Discovery, 2003, vol. 2, pp. 289-294.
Granhall, Charlotte et al., "Safety and Pharmacokinetics of Single and Multiple Ascending Doses of the Novel Oral Human GLP-1 Analogue, Oral Semaglutide, in Healthy Subjects and Subjects with Type 2 Diabetes" Clinical Pharmacokinetics, published Dec. 18, 2018.
Hellriegel, Edward T. et al., "Interpatient variability in bioavailability is related to the extent of absorption: Implications for bioavailability and bioequivalence studies" Clinical Pharmacology & Therapeutics, Dec. 1996, vol. 60, No. 6, pp. 601-607.

US 11,759,502 B2

COMPOSITIONS OF GLP-1 PEPTIDES AND PREPARATION THEREOF

CROSS-REFERENCE TO RELATED APPLICATIONS

This application is a continuation of U.S. application Ser. No. 17/157,363, filed Jan. 25, 2021 which is a continuation of a U.S. application Ser. No. 14/386,589, filed Sep. 19, 2014, issued as U.S. Pat. No. 10,933,120, granted on Mar. 2, 2021, which is a 35 U.S.C. § 371 National Stage application of International Application PCT/EP2013/055362 (WO 2013/139694), filed Mar. 15, 2013, which claims priority to European Patent Application 12160743.6, filed Mar. 22, 2012, and to European Patent Application 13153459.6, filed Jan. 31, 2013; this application claims priority under 35 U.S.C. § 119 to U.S. Provisional Application 61/748,840, filed Jan. 4, 2013; the contents of which are incorporated by reference in their entirety.

The present invention is directed to compositions comprising pharmacologically active agents, such as GLP-1, and a delivery agent as well as processes for their preparation and use thereof in medicine.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Mar. 24, 2022, is named 8481US04_SeqList_ST25.txt and is 2 kilobytes in size.

BACKGROUND

One of the main challenges in oral delivery of proteins and peptides is the inability of these compounds to be readily transported across the membranes of the gastrointestinal tract. The delivery agent SNAC has previously been shown to improve the bioavailability of orally administered peptides. The present invention relates to further improvements of the bioavailability by oral administration of compositions of such peptides, in particular of GLP-1 peptides.

SUMMARY

In one embodiment the invention relates to a pharmaceutical composition comprising a first type and a second type of granules, wherein said first type of granules comprises a salt of N-(8-(2-hydroxybenzoyl)amino)caprylic acid and no GLP-1 peptide, and wherein said second type of granules comprises a GLP-1 peptide and no salt of N-(8-(2-hydroxybenzoyl)amino)caprylic acid. In some embodiments the term "granule" refers to small particles gathered into a large mass.

In one embodiment the invention relates to a process of producing a pharmaceutical composition comprising a salt of N-(8-(2-hydroxybenzoyl)amino)caprylic acid and a GLP-1 peptide, wherein the process comprises the steps: a) mixing a GLP-1 peptide with a filler and/or a binder; b) dry granulation of the mixture of step a; c) mixing the granules obtained in step b with a composition comprising a salt of N-(8-(2-hydroxybenzoyl)amino) caprylic acid; and d) optionally adding further lubricant, wherein the mixture of step a does not comprise a salt of N-(8-(2-hydroxybenzoyl)amino) caprylic acid.

In one embodiment the invention relates to a process of producing a pharmaceutical composition comprising a salt of N-(8-(2-hydroxybenzoyl)amino)caprylic acid and a GLP-1 peptide, wherein the process comprises the steps: a) mixing a salt of N-(8-(2-hydroxybenzoyl)amino)caprylic acid with a lubricant and/or a filler; b) dry granulation of the mixture of step a; c) mixing the granules obtained in step b with a composition comprising a GLP-1 peptide; and d) optionally adding further lubricant, wherein the mixture of step a does not comprise a GLP-1 peptide.

In one embodiment the invention relates to a process of producing a pharmaceutical composition comprising a salt of N-(8-(2-hydroxybenzoyl)amino)caprylic acid and a GLP-1 peptide, wherein the process comprises the steps: a) mixing a GLP-1 peptide with a filler and/or a binder; b) dry granulation of the mixture of step a; c) mixing a salt of N-(8-(2-hydroxybenzoyl)amino)caprylic acid, optionally a lubricant and/or a filler; d) dry granulation of the mixture of step c; e) mixing the granules obtained in step b with the granules obtained in step d; and f) optionally adding further lubricant, wherein the mixture of step a does not comprise a salt of N-(8-(2-hydroxybenzoyl)amino) caprylic acid and wherein the mixture of step c does not comprise a GLP-1 peptide.

In one embodiment the invention relates to a granule comprising a salt of N-(8-(2-hydroxybenzoyl)amino) caprylic acid, a lubricant, optionally a filler, and no GLP-1 peptide. In one embodiment the invention relates to a process of producing a granule comprising a salt of N-(8-(2-hydroxybenzoyl)amino)caprylic acid, wherein the process comprises the steps: a) mixing a salt of N-(8-(2-hydroxybenzoyl)amino)caprylic acid (such as SNAC) with a lubricant and/or a filler; and b) dry granulation of the mixture of step a, wherein the mixture of step a does not comprise a GLP-1 peptide.

In one embodiment the invention relates to a granule comprising a GLP-1 peptide, a filler, a binder, and no salt of N-(8-(2-hydroxybenzoyl)amino)caprylic acid. In one embodiment the invention relates to a process of producing a granule comprising a GLP-1 peptide, wherein the process comprises the steps: a) mixing a GLP-1 peptide, optionally a filler and/or a binder; and b) roller compacting the mixture of step a, wherein the mixture of step a does not comprise a salt of N-(8-(2-hydroxybenzoyl)amino) caprylic acid.

In one embodiment the invention relates to a pharmaceutical composition or a granule obtained by the process as defined herein.

In one embodiment the invention relates to a composition or a granule as defined herein for use in medicine, such as for treatment of diabetes or obesity, wherein said composition is administered orally. In one embodiment the invention relates to a method for treatment of diabetes or obesity comprising administering the composition as defined herein to a patient in need thereof, wherein said composition is administered orally.

DESCRIPTION

The present inventors surprisingly found that the dissolution properties of tablets manufactured from the same composition (i.e. same type and the same amounts of excipients and delivery agent) was determined by the design of the granules from which the tablets were formed.

Furthermore, the present inventors found that the dissolution behaviour surprisingly had a marked effect on the bioavailability of GLP-1 peptide from the composition, such as the tablet. Thus, the present inventors have shown that the bioavailability of solid tablets manufactured from various granule designs can be predicted from in vitro data, i.e. dissolution data. In one embodiment this invention provides compositions, granules and methods for their preparation with improved bioavailability of the GLP-1 peptide.

Generally, the term "bioavailability" as used herein refers to the fraction of an administered dose of an active pharmaceutical ingredient (API) and/or active moieties, such as a GLP-1 peptide as defined herein, which reaches the systemic circulation un-changed or in another active form. By definition, when an API and/or active moieties are administered intravenously, its bioavailability is 100%. However, when it is administered via other routes (such as orally), its bioavailability decreases (due to incomplete absorption and/or first-pass metabolism). Knowledge about bioavailability is important when calculating dosages for non-intravenous routes of administration.

Absolute oral bioavailability is calculated as the relative exposure of the API and/or active moieties in systemic circulation following oral administration (estimated as the area under the plasma concentration versus time curve) compared to the exposure of the API following intravenous administration.

Pharmaceutical Compositions

In some embodiments the invention relates to a pharmaceutical composition comprising a first type and a second type of granules, wherein said first type of granules comprises a salt of N-(8-(2-hydroxybenzoyl)amino)caprylic acid and said second type of granules comprises a GLP-1 peptide. In some embodiments the first type of granules further comprises a lubricant, such as magnesium stearate. In some embodiments the first type of granules further comprises a filler, such as microcrystalline cellulose. Accordingly, the first type of granules may further comprise a lubricant and optionally a filler. In some embodiments the second type of granules further comprises a filler, such as microcrystalline cellulose. In some embodiments the second type of granules further comprises a binder, such as povidone. Accordingly, the second type of granules may further comprise a filler and optionally a binder. In some embodiments the composition further comprises an extragranular lubricant, such as magnesium stearate.

In some embodiments N-(8-(2-hydroxybenzoyl)amino) caprylic acid is referred to as "NAC".

In some embodiments the first type of granules comprising a salt of N-(8-(2-hydroxybenzoyl)amino)caprylic acid does not contain a GLP-1 peptide. In some embodiments the second type of granules comprising a GLP-1 peptide does not contain a salt of N-(8-(2-hydroxybenzoyl)amino) caprylic acid. In some embodiments the pharmaceutical composition comprises a first type and a second type of granules, wherein said first type of granules comprises a salt of N-(8-(2-hydroxybenzoyl)amino)caprylic acid and no GLP-1 peptide, and wherein said second type of granules comprises a GLP-1 peptide and no salt of N-(8-(2-hydroxybenzoyl)amino)caprylic acid.

In some embodiments the term "granule" refers to particles gathered into larger particles.

In some embodiments the invention relates to a pharmaceutical composition comprising a salt of N-(8-(2-hydroxybenzoyl)amino)caprylic acid and a GLP-1 peptide, wherein the release of said salt of N-(8-(2-hydroxybenzoyl)amino) caprylic acid is simultaneous with or faster than the release of said GLP-1 peptide as determined by dissolution testing using Assay (I). In some embodiments the invention relates to a pharmaceutical composition comprising a salt of N-(8-(2-hydroxybenzoyl)amino)caprylic acid and a GLP-1 peptide, wherein the release of said salt of N-(8-(2-hydroxybenzoyl)amino)caprylic acid is simultaneous with or faster than the release of said GLP-1 peptide.

In some embodiments the term "release" when used with reference to N-(8-(2-hydroxybenzoyl)amino)caprylic acid and optionally compared to release of GLP-1 peptide is determined within 30 minutes, such as within 25, 20, 15 minutes, or such as within 10 or 5 minutes, as determined by dissolution testing using Assay (I). Accordingly, the release may be determined within 30 minutes of dissolution testing using Assay (I). In some embodiments the release of said salt of N-(8-(2-hydroxybenzoyl)amino)caprylic acid when referred to as "faster than" the release of said GLP-1 peptide is determined within 30 minutes, such as within 25, 20, 15 minutes, or such as within 10 or 5 minutes, as determined by dissolution testing using Assay (I). In some embodiments the release of said salt of N-(8-(2-hydroxybenzoyl)amino) caprylic acid when referred to as "faster than" the release of said GLP-1 peptide is determined within 30 minutes, such as within 25, 20, 15 minutes, or such as within 10 or 5 minutes, as determined by dissolution testing using Assay (I) at pH 2.5.

In some embodiments the release of said salt of N-(8-(2-hydroxybenzoyl)amino)caprylic acid when referred to as "simultaneous with" the release of said GLP-1 peptide is determined within 30 minutes, such as within 25, 20, 15 minutes, or such as within 10 or 5 minutes, as determined by dissolution testing using Assay (I). In some embodiments the release of said salt of N-(8-(2-hydroxybenzoyl)amino) caprylic acid when referred to as "simultaneous with" the release of said GLP-1 peptide is determined within 30 minutes, such as within 25, 20, 15 minutes, or such as within 10 or 5 minutes, as determined by dissolution testing using Assay (I) at pH 2.5.

In some embodiments the invention relates to a pharmaceutical composition according to any one of the preceding claims, wherein the amount of dissolved salt of N-(8-(2-hydroxybenzoyl)amino)caprylic acid peaks within the first 60 minutes as determined by dissolution testing using Assay (I) at pH 2.5. In some embodiments the invention relates to a pharmaceutical composition, wherein the amount of dissolved salt of N-(8-(2-hydroxybenzoyl)amino)caprylic acid peaks within the first 30 minutes as determined by dissolution testing using Assay (I) at pH 2.5. In some embodiments the amount of dissolved salt of N-(8-(2-hydroxybenzoyl) amino)caprylic acid peaks within 55 minutes, such as within 50, 45 or 40 minutes, as determined by dissolution testing using Assay (I) at pH 2.5. In some embodiments the amount of dissolved salt of N-(8-(2-hydroxybenzoyl)amino)caprylic acid peaks within 39 or 38 minutes, such as within 37, 36, or 35 minutes, as determined by dissolution testing using Assay (I) at pH 2.5. In some embodiments the amount of dissolved salt of N-(8-(2-hydroxybenzoyl)amino)caprylic acid peaks within 34 minutes, such as within 33, 32, or 31 minutes, as determined by dissolution testing using Assay (I) at pH 2.5. In some embodiments the amount of dissolved salt of N-(8-(2-hydroxybenzoyl)amino)caprylic acid peaks within 31 minutes, such as within 32, 33, 34, 35, 36, 37, 38, 39, 40, 45, 50, 55, or 60 minutes as determined by dissolution testing using Assay (I) at pH 2.5.

In some embodiments the composition comprises granules which have been manufactured by dry granulation. In some embodiments the composition comprises granules which have been manufactured by roller compaction. In some embodiments the moldings from the roller compactions process are comminuted into granules. As used herein the term "composition" refers to a pharmaceutical composition.

In some embodiments the composition is in the form of a solid dosage form. In some embodiments the composition is in the form of a tablet. In some embodiments the composition is in the form of a capsule. In some embodiments the composition is in the form of a sachet.

In some embodiments the composition or granule comprises at least one pharmaceutically acceptable excipient. The term "excipient" as used herein broadly refers to any component other than the active therapeutic ingredient(s). The excipient may be an inert substance, which is inert in the sense that it substantially does not have any therapeutic and/or prophylactic effect per se. The excipient may serve various purposes, e.g. as a delivery agent, absorption enhancer, vehicle, filler (also known as diluents), binder, lubricant, glidant, disintegrant, crystallization retarders, acidifying agent, alkalizing agent, preservative, antioxidant, buffering agent, chelating agent, complexing agents, surfactant agent, emulsifying and/or solubilizing agents, sweetening agents, wetting agents stabilizing agent, colouring agent, flavouring agent, and/or to improve administration, and/or absorption of the active substance. A person skilled in the art may select one or more of the aforementioned excipients with respect to the particular desired properties of the solid oral dosage form by routine experimentation and without any undue burden. The amount of each excipient used may vary within ranges conventional in the art. Techniques and excipients which may be used to formulate oral dosage forms are described in Handbook of Pharmaceutical Excipients, 6th edition, Rowe et al., Eds., American Pharmaceuticals Association and the Pharmaceutical Press, publications department of the Royal Pharmaceutical Society of Great Britain (2009); and Remington: the Science and Practice of Pharmacy, 21th edition, Gennaro, Ed., Lippincott Williams & Wilkins (2005).

In some embodiments the composition or granule comprises a filler, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), other cellulose derivatives, sucrose, sorbitol, mannitol, dextrins, dextrans, maltodextrins, dextrose, fructose, kaolin, mannitol, sorbitol, sucrose, sugar, starches or modified starches (including potato starch, maize starch and rice starch), calcium phosphate (e.g. basic calcium phosphate, calcium hydrogen phosphate, dicalcium phosphate hydrate), calcium sulphate, calcium carbonate, or sodium alginate. In some embodiments the filler is microcrystalline cellulose, such as Avicel PH 101.

In some embodiments the composition or granule comprises a binder, such as lactose (e.g. spray-dried lactose, α-lactose, β-lactose, Tabletose®, various grades of Pharmatose®, Microtose® or Fast-FloC®), microcrystalline cellulose (various grades of Avicel®, Elcema®, Vivacel®, Ming Tai® or Solka-Floc®), hydroxypropylcellulose, L-hydroxypropylcellulose (low-substituted), hypromellose (HPMC) (e.g. Methocel E, F and K, Metolose SH of Shin-Etsu, Ltd, such as, e.g., the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, ethylcellulose, sodium carboxymethylcellulose, other cellulose derivatives, sucrose, dextrins, maltodextrins, starches or modified starches (including potato starch, maize starch and rice starch), calcium lactate, calcium carbonate, acacia, sodium alginate, agar, carrageenan, gelatin, guar gum, pectin, PEG, or povidone. In some embodiments the binder is povidone, such as povidone K 90.

In some embodiments the composition or granule comprises a disintegrant, such as alginic acid, alginates, microcrystalline cellulose, hydroxypropyl cellulose, other cellulose derivatives, croscarmellose sodium, crospovidone, polacrillin potassium, sodium starch glycolate, starch, pregelatinized starch, or carboxymethyl starch (e.g. Primogel® and Explotab®).

In some embodiments the composition or granule comprises a lubricant, such as stearic acid, magnesium stearate, calcium stearate or other metallic stearate, talc, waxes, glycerides, light mineral oil, glyceryl behenate, hydrogenated vegetable oils, sodium stearyl fumarate, polyethylene glycols, alkyl sulfates, or sodium benzoate. In some embodiments the composition or granule comprises a lubricant, such as magnesium silicate, talc, or colloidal silica. In some embodiments the lubricant is magnesium stearate.

In some embodiments the composition or granule comprises one or more excipients selected from crystallization retarders, such as Povidone, etc.; solubilizing agents (also known as surfactants), such as anionic surfactants (e.g. Pluronic or Povidone), cationic surfactants, nonionic surfactants, and/or zwitterionic surfactants; colouring agents, including dyes and pigments, such as Iron Oxide Red or Yellow, titanium dioxide, and/or talc; and/or pH control agents, such as citric acid, tartaric acid, fumaric acid, sodium citrate, dibasic calcium phosphate, and/or dibasic sodium phosphate.

In some embodiments the composition comprises at least 60% (w/w) delivery agent, less than 10% (w/w) binder, 5-40% (w/w) filler, and less than 10% (w/w) lubricant.

In some embodiments the composition comprises at least 60% (w/w), such as 65-75% (w/w), 60-80% (w/w), or 50-90% (w/w), delivery agent. In some embodiments the composition comprises at least 70% (w/w), such as 70-80% (w/w), delivery agent.

In some embodiments the composition comprises 0.1-10% (w/w), such as 0.2-4% (w/w) or 0.5-3% (w/w), binder. In some embodiments the composition comprises 1.5-2.5% (w/w), such as 1.7-2.3% (w/w), 1.8-2.2% (w/w), or 1.9-2.1% (w/w), binder. In some embodiments the composition comprises 1% (w/w) or 2% (w/w) binder.

In some embodiments the composition comprises 5-40% (w/w), such as 10-30% (w/w) or 5-25% (w/w), filler. In some embodiments the composition comprises 10-25% (w/w), such as 17-23% (w/w), 18-22% (w/w), or 19-21% (w/w), filler. In some embodiments the composition comprises 10.9% (w/w) or 18% (w/w) filler, or comprises 19.5% (w/w) or 20.5 (w/w) filler.

In some embodiments the composition comprises 0.1-10% (w/w) or 0.5-5% (w/w), such as 1-3.5% (w/w) or 1% (w/w), lubricant. In some embodiments the composition comprises 1.5-3% (w/w), such as 2.1-2.7% (w/w), 2.2-2.6% (w/w) or 2.3-2.5% (w/w), lubricant.

Still further, the composition or granule of the invention may be formulated as is known in the art of oral formulations of insulinotropic compounds.

The composition or granule may be administered in several dosage forms, for example as a tablet; a capsule such as hard capsules, sachet or a powder. The composition or granule may further be compounded in a drug carrier or drug delivery system, e.g. in order to improve stability and/or solubility or further improve bioavailability.

In some embodiments the weight of the tablet is in the range of 150 mg to 1000 mg, such as in the range of 300-600 mg or 350-450 mg.

In some embodiments the invention relates to a first granule comprising at least 75% (w/w) delivery agent, less than 10% (w/w) lubricant, and optionally less than 20% filler and no GLP-1 peptide. In some embodiments the invention relates to a first granule comprising at least 80% (w/w) delivery agent, less than 10% (w/w) lubricant, and optionally less than 20% filler and no GLP-1 peptide. In some embodiments the first granule comprises 75-90% (w/w), such as 78-88% (w/w), 80-86% (w/w) or 82-84% (w/w), delivery agent. In some embodiments the first granule comprises less than 10% (w/w), such as 1-3% (w/w), 1.5-2.5% (w/w) or 1.9-2.3% (w/w), lubricant, In some embodiments the first granule comprises less than 20%, such as 10-20% (w/w), 12-18% (w/w) or 14-17% (w/w), filler. In some embodiments the first granule comprises no GLP-1 peptide. In some embodiments the granule comprises at least 80% (w/w) delivery agent, less than 10% (w/w) lubricant, and optionally less than 20% filler.

In some embodiments the invention relates to a second granule comprising a GLP-1 peptide, at least 15% (w/w) filler and less than 40% (w/w) binder and no salt of N-(8-(2-hydroxybenzoyl)amino)caprylic acid. In some embodiments the second granule comprises at least 1%, such as 1-70% (w/w), 2-40% (w/w) or 4-30% (w/w), GLP-1 peptide. In some embodiments the second granule comprises at least 20%, such as 40-80% (w/w) or 50-75% (w/w), filler. In some embodiments the second granule comprises less than 30%, such as 5-30% (w/w), 10-28% (w/w) or 15-25% (w/w), binder. In some embodiments the second granule comprises no salt of N-(8-(2-hydroxybenzoyl)amino) caprylic acid. In some embodiments the granule comprises a GLP-1 peptide, at least 15% (w/w) filler and less than 40% (w/w) binder. In some embodiments the granule comprises a GLP-1 peptide, at least 50% (w/w) filler and less than 40% (w/w) binder.

In some embodiments the invention relates to a composition comprising a first and a second type of granules, wherein the first type of granule comprises at least 75% (w/w) delivery agent, less than 10% (w/w) lubricant, optionally less than 20% filler and no GLP-1 peptide, and wherein the second type of granule comprises a GLP-1 peptide, at least 15% (w/w) filler, less than 40% (w/w) binder and no salt of N-(8-(2-hydroxybenzoyl)amino)caprylic acid. In some embodiments the invention relates to a composition comprising a first and a second type of granules, wherein the first type of granule comprises at least 75% (w/w) delivery agent, less than 10% (w/w) lubricant, less than 20% filler and no GLP-1 peptide, and wherein the second type of granule comprises a GLP-1 peptide, at least 15% (w/w) filler, less than 40% (w/w) binder and no salt of N-(8-(2-hydroxybenzoyl)amino)caprylic acid. In some embodiments the invention relates to a composition comprising a first and a second type of granules, wherein the first type of granule comprises at least 75% (w/w) delivery agent, less than 10% (w/w) lubricant, and no GLP-1 peptide, and wherein the second type of granule comprises a GLP-1 peptide, at least 15% (w/w) filler, less than 40% (w/w) binder and no salt of N-(8-(2-hydroxybenzoyl)amino)caprylic acid.

Methods of Preparation of Pharmaceutical Compositions

The composition of the invention may be prepared as is known in the art. In some embodiments the composition or the granule may be prepared as described in the examples herein. In some embodiments the composition may be granulated prior to being compressed into tablets. In some embodiments the granules of the invention are manufactured by dry granulation, such as by roller compaction compaction. In some embodiments the moldings from the roller compactions process are comminuted into granules. The composition may comprise one or more intragranular parts and an extragranular part, wherein the intragranular parts have been granulated, and wherein the extragranular part has been added after granulation. A first intragranular part may comprise the GLP-1 peptide and one or more excipients, and a second intragranular part may comprise the delivery agent and optionally one or more excipients. A first intragranular part may comprise the GLP-1 peptide, filler and/or a binder and a second intragranular part may comprise the delivery agent, lubricant and filler. The first intragranular part may comprise the GLP-1 peptide, filler and/or binder and a second intragranular part may comprise the delivery agent, lubricant and/or filler. In some embodiments the first intragranular part comprises the GLP-1 agonist (i.e. the GLP-1 peptide), microcrystalline cellulose and/or povidone and the second intragranular part comprises the delivery agent, magnesium stearate and microcrystalline cellulose. In some embodiments the first intragranular part comprises the GLP-1 agonist (i.e. the GLP-1 peptide), microcrystalline cellulose and/or povidone and the second intragranular part comprises the delivery agent, magnesium stearate and/or microcrystalline cellulose. The extragranular part may comprise a lubricant. In some embodiments the extragranular part comprises magnesium stearate. In some embodiments the term "filler and/or binder" or "filler and/or a binder" refers to a filler and optionally a binder. In some embodiments the term "lubricant and filler" or "lubricant and/or filler" refers to a lubricant and optionally a filler.

To prepare a dry blend of tabletting material, the various components are weighed, optionally delumped and then combined. The mixing of the components may be carried out until a homogeneous blend is obtained.

If granules are to be used in the tabletting material, granules may be produced in a manner known to a person skilled in the art, for example by dry granulation techniques in which the pharmaceutically active agent and/or delivery agents are compacted with the excipients to form relatively large moldings, for example slugs or ribbons, which are comminuted by grinding, and the ground material serves as the tabletting material to be later compressed into tablets. Suitable equipment for dry granulation includes but is not limited to roller compaction equipment from Gerteis, such as Gerteis MINI-PACTOR.

To compress the tabletting material into a solid oral dosage form, for example a tablet, a tablet press may be used. In a tabletting press, the tabletting material is filled (e.g. force fed or gravity fed) into a die cavity. The tabletting material is then compressed by a punch with pressure. Subsequently, the resulting compact, or tablet is ejected from the tabletting press. The above mentioned compression process is subsequently referred to herein as the "compression process". Suitable tablet presses include, but are not limited to, rotary tablet presses and eccentric tablet presses. Examples of tablet presses include, but are not limited to, the Fette 102i (Fette GmbH), the Korsch XL100, the Korsch PH 106 rotary tablet press (Korsch AG, Germany), the Korsch EK-O eccentric tabletting press (Korsch AG, Germany) and the Manesty F-Press (Manesty Machines Ltd., United Kingdom).

In some embodiments the method of preparation of the tablet comprises i) dry granulation of a mixture comprising the GLP-1 agonist (i.e. the GLP-1 peptide), filler and a binder; ii) dry granulation of a mixture comprising the delivery agent, lubricant and filler; iii) mixing of the granules with a lubricant; and then iv) compression of the blend into tablets. In some embodiments the method of preparation of the tablet comprises i) dry granulation of a mixture comprising the GLP-1 agonist (i.e. the GLP-1 peptide), filler and a binder; ii) dry granulation of a mixture comprising the delivery agent, lubricant and/or filler; iii) mixing of the granules with a lubricant; and then iv) compression of the blend into tablets.

In some embodiments the invention relates to a process of producing a pharmaceutical composition comprising a salt of N-(8-(2-hydroxybenzoyl)amino)caprylic acid and a GLP-1 peptide, wherein the process comprises the steps: a) mixing a GLP-1 peptide with a filler and/or a binder; b) dry granulation of the mixture of step a; c) mixing the granules obtained in step b with a composition comprising a salt of N-(8-(2-hydroxybenzoyl)amino) caprylic acid; and d) optionally adding further lubricant. In some embodiments the invention relates to a process of producing a pharmaceutical composition comprising a salt of N-(8-(2-hydroxybenzoyl)amino)caprylic acid and a GLP-1 peptide, wherein the process comprises the steps: a) mixing a salt of N-(8-(2-hydroxybenzoyl)amino)caprylic acid with a lubricant and/or a filler; b) dry granulation of the mixture of step a; c) mixing the granules obtained in step b with a composition comprising a GLP-1 peptide; and d) optionally adding further lubricant. In some embodiments the invention relates to a process of producing a pharmaceutical composition comprising a salt of N-(8-(2-hydroxybenzoyl)amino) caprylic acid and a GLP-1 peptide, wherein the process comprises the steps: a) mixing a GLP-1 peptide with a filler and/or a binder; b) dry granulation of the mixture of step a; c) mixing a salt of N-(8-(2-hydroxybenzoyl)amino)caprylic acid, optionally a lubricant and/or a filler; d) dry granulation of the mixture of step c; e) mixing the granules obtained in step b with the granules obtained in step d; and f) optionally adding further lubricant.

In one embodiment the invention relates to a process of producing a pharmaceutical composition comprising a salt of N-(8-(2-hydroxybenzoyl)amino)caprylic acid and a GLP-1 peptide, wherein the process comprises the steps: a) mixing a GLP-1 peptide with a filler and/or a binder; b) dry granulation of the mixture of step a; c) mixing a salt of N-(8-(2-hydroxybenzoyl)amino)caprylic acid, optionally a lubricant and/or a filler; d) dry granulation of the mixture of step c; e) mixing the granules obtained in step b with the granules obtained in step d; and f) optionally adding further lubricant, wherein the mixture of step a does not comprise a salt of N-(8-(2-hydroxybenzoyl)amino) caprylic acid and wherein the mixture of step c does not comprise a GLP-1 peptide.

In one embodiment the invention relates to a granule comprising a salt of N-(8-(2-hydroxybenzoyl)amino) caprylic acid, a lubricant, optionally a filler, and no GLP-1 peptide. In one embodiment the invention relates to a process of producing a granule comprising a salt of N-(8-(2-hydroxybenzoyl)amino)caprylic acid, wherein the process comprises the steps: a) mixing a salt of N-(8-(2-hydroxybenzoyl)amino)caprylic acid (such as SNAC) with a lubricant and/or a filler; and b) dry granulation of the mixture of step a, wherein the mixture of step a does not comprise a GLP-1 peptide.

In one embodiment the invention relates to a granule comprising a GLP-1 peptide, a filler, a binder, and no salt of N-(8-(2-hydroxybenzoyl)amino)caprylic acid. In one embodiment the invention relates to a process of producing a granule comprising a GLP-1 peptide, wherein the process comprises the steps: a) mixing a GLP-1 peptide, optionally a filler and/or a binder; and b) roller compacting the mixture of step a, wherein the mixture of step a does not comprise a salt of N-(8-(2-hydroxybenzoyl)amino) caprylic acid.

In some embodiments the mixing step comprising mixing of a salt of N-(8-(2-hydroxybenzoyl)amino)caprylic acid with a lubricant and/or a filler prior to dry granulation has a duration of at least 20 minutes. In some embodiments the mixing step comprising mixing of a salt of N-(8-(2-hydroxybenzoyl)amino)caprylic acid with a lubricant and/or a filler prior to dry granulation has a duration of at least 30 minutes or at least 40 minutes, such as 50 minutes. In some embodiments the mixing step comprising mixing of the first type of granules comprising a GLP-1 peptide with the second type of granules comprising a salt of N-(8-(2-hydroxybenzoyl) amino)caprylic acid has a duration of at least 15 minutes or at least 20 minutes, such as at least 25 minutes or at least 30 minutes.

In some embodiments the invention relates to a pharmaceutical composition obtained by the process as defined herein.

In some embodiments the invention relates to a granule comprising a salt of N-(8-(2-hydroxybenzoyl)amino) caprylic acid and a lubricant. In some embodiments the granule comprises a salt of N-(8-(2-hydroxybenzoyl)amino) caprylic acid, a lubricant, and a filler. In some embodiments the invention relates to a granule comprising a GLP-1 peptide, a filler and a binder. In some embodiments the granule is prepared according to the process as defined herein.

In some embodiments the invention relates to a process of producing a granule comprising a salt of N-(8-(2-hydroxybenzoyl)amino)caprylic acid, wherein the process comprises the steps: a) mixing a salt of N-(8-(2-hydroxybenzoyl)amino)caprylic acid (such as SNAC) with a lubricant and/or a filler; and b) dry granulation of the mixture of step a. In some embodiments the mixing step comprising mixing of a salt of N-(8-(2-hydroxybenzoyl)amino) caprylic acid with a lubricant and/or a filler prior to dry granulation has a duration of at least 20 minutes. In some embodiments the mixing step comprising mixing of a salt of N-(8-(2-hydroxybenzoyl)amino) caprylic acid with a lubricant and/or a filler prior to dry granulation has a duration of at least 30 minutes or at least 40 minutes, such as 50 minutes.

In some embodiments the invention relates to a process of producing a granule comprising a GLP-1 peptide, wherein the process comprises the steps: a) mixing a GLP-1 peptide, optionally a filler and/or a binder; and b) roller compacting the mixture of step a.

In some embodiments the invention relates to a granule obtained by the process as defined herein.

In some embodiments the lubricant is magnesium stearate. In some embodiments the filler is microcrystalline cellulose. In some embodiments the binder is povidone.

In some embodiments the term "resistance to crushing of tablets" has the meaning defined in section 2.9.8 in the European Pharmacopoeia 7.5, 7th edition 2012; resistance to crushing may be measured inter alia in Newton (N) or kilopond (kP) using a jaw speed of 20 N/s (1 kP equals 9.807 N).

In some embodiments the term "roller compaction force" means the force between the rolls of the roller compactor when compacting materials into a continuous strip of compressed material as determined by a pressure transducer that converts the hydraulic pressure into electrical signal; the roller compaction force may be measured in kiloNewton (kN) or in kiloNewton per roll width (kN/cm).

In Vitro Methods

Dissolution of compositions of the invention may be determined as described in Assay (I) herein. In some embodiments the dissolution testing using Assay (I) is carried out at any one of pH 1.0-8.0. In some embodiments the dissolution testing using Assay (I) is carried out at pH 1.0. In some embodiments the dissolution testing using Assay (I) is carried out at pH 2.5. In some embodiments the dissolution testing using Assay (I) is carried out at pH 6.8.

GLP-1 Peptides

In one embodiment the composition of the invention comprises a GLP-1 peptide. The term "GLP-1 peptide" as used herein refers to a compound, which fully or partially activates the human GLP-1 receptor. In some embodiments the "GLP-1 peptide" binds to a GLP-1 receptor, e.g., with an affinity constant ($K_D$) or activate the receptor with a potency ($EC_{50}$) of below 1 μM, e.g. below 100 nM as measured by methods known in the art (see e.g. WO 98/08871) and exhibits insulinotropic activity, where insulinotropic activity may be measured in vivo or in vitro assays known to those of ordinary skill in the art. For example, the GLP-1 peptide may be administered to an animal with increased blood glucose (e.g. obtained using an Intravenous Glucose Tolerance Test (IVGTT), a person skilled in the art will be able to determine a suitable glucose dosage and a suitable blood sampling regime, e.g. depending on the species of the animal, for the IVGTT) and the plasma insulin concentration measured over time. In some embodiments the GLP-1 peptide is referred to as a GLP-1 agonist.

In some embodiments the GLP-1 peptide is a GLP-1 analogue, optionally comprising one substituent. The term "analogue" as used herein referring to a GLP-1 peptide (hereafter "peptide") means a peptide wherein at least one amino acid residue of the peptide has been substituted with another amino acid residue and/or wherein at least one amino acid residue has been deleted from the peptide and/or wherein at least one amino acid residue has been added to the peptide and/or wherein at least one amino acid residue of the peptide has been modified. Such addition or deletion of amino acid residues may take place at the N-terminal of the peptide and/or at the C-terminal of the peptide. In some embodiments a simple nomenclature is used to describe the GLP-1 peptide, e.g., [Aib8] GLP-1(7-37) designates an analogue of GLP-1(7-37) wherein the naturally occurring Ala in position 8 has been substituted with Aib. In some embodiments the GLP-1 peptide comprises a maximum of twelve, such as a maximum of 10, 8 or 6, amino acids which have been alterered, e.g., by substitution, deletion, insertion and/or modification, compared to e.g. GLP-1(7-37). In some embodiments the analogue comprises up to 10 substitutions, deletions, additions and/or insertions, such as up to 9 substitutions, deletions, additions and/or insertions, up to 8 substitutions, deletions, additions and/or insertions, up to 7 substitutions, deletions, additions and/or insertions, up to 6 substitutions, deletions, additions and/or insertions, up to 5 substitutions, deletions, additions and/or insertions, up to 4 substitutions, deletions, additions and/or insertions or up to 3 substitutions, deletions, additions and/or insertions, compared to e.g. GLP-1(7-37). Unless otherwise stated the GLP-1 comprises only L-amino acids.

In some embodiments the term "GLP-1 analogue" or "analogue of GLP-1" as used herein refers to a peptide, or a compound, which is a variant of the human Glucagon-Like Peptide-1 (GLP-1(7-37)). GLP-1(7-37) has the sequence HAEGTFTSDV SSYLEGQAAKEFIAWLVKGRG (SEQ ID No: 1). In some embodiments the term "variant" refers to a compound which comprises one or more amino acid substitutions, deletions, additions and/or insertions.

In one embodiment the GLP-1 peptide exhibits at least 60%, 65%, 70%, 80% or 90% sequence identity to GLP-1 (7-37) over the entire length of GLP-1(7-37). As an example of a method for determination of sequence identity between two analogues the two peptides [Aib8]GLP-1(7-37) and GLP-1(7-37) are aligned. The sequence identity of [Aib8] GLP-1(7-37) relative to GLP-1(7-37) is given by the number of aligned identical residues minus the number of different residues divided by the total number of residues in GLP-1 (7-37). Accordingly, in said example the sequence identity is (31−1)/31.

In one embodiment the C-terminal of the GLP-1 peptide is an amide.

In some embodiments the GLP-1 peptide is GLP-1(7-37) or GLP-1(7-36)amide. In some embodiments the GLP-1 peptide is exendin-4, the sequence of which is (SEQ ID No: 2)
HGEGTFITSDLSKQMEEEAVRLFIEWLKNGGPSSGAPPPS.

In some embodiments the GLP-1 peptide comprises one substituent which is covalently attached to the peptide. In some embodiments the substituent comprises a fatty acid or a fatty diacid. In some embodiments the substituent comprises a C16, C18 or C20 fatty acid. In some embodiments the substituent comprises a C16, C18 or C20 fatty diacid. In some embodiments the substituent comprises formula (X)

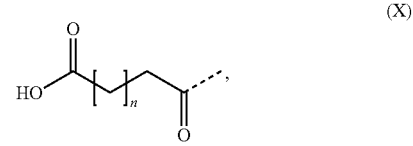

(X)

wherein n is at least 13, such as n is 13, 14, 15, 16, 17, 18 or 19. In some embodiments the substituent comprises formula (X), wherein n is in the range of 13 to 19, such as in the range of 13 to 17. In some embodiments the substituent comprises formula (X), wherein n is 13, 15 or 17. In some embodiments the substituent comprises formula (X), wherein n is 13. In some embodiments the substituent comprises formula (X), wherein n is 15. In some embodiments the substituent comprises formula (X), wherein n is 17. In some embodiments the substituent comprises one or more 8-amino-3,6-dioxaoctanoic acid (OEG), such as two OEG.

In some embodiments the substituent is [2-(2-{2-[2-(2-{2-[(S)-4-carboxy-4-(17-carboxyheptadecanoylamino) butyrylamino]ethoxy}ethoxy)acetylamino]ethoxy}ethoxy) acetyl].

In some embodiments the substituent is [2-(2-{2-[2-(2-{2-[(S)-4-carboxy-4-({trans-4-[(19-carboxynonadecanoylamino)methyl]cyclohexanecarbonyl}amino)butyrylamino] ethoxy}ethoxy)acetylamino]ethoxy}ethoxy)acetyl].

In some embodiments the GLP-1 peptide is semaglutide, also known as N-epsilon26-[2-(2-{2-[2-(2-{2-[(S)-4-carboxy-4-(17-carboxyheptadecanoylamino) butyrylamino] ethoxy}ethoxy)acetylamino]ethoxy}ethoxy)acetyl][Aib8, Arg34]GLP-1(7-37), which may be prepared as described in WO2006/097537, Example 4.

In some embodiments the composition comprises the GLP-1 peptide or a pharmaceutically acceptable salt, amide, or ester thereof. In some embodiments the composition comprises the GLP-1 peptide one or more pharmaceutically acceptable counter ions.

In some embodiments the dosage of GLP-1 peptide is in the range of 0.01 mg to 100 mg. In some embodiments the composition or granule comprises an amount of a GLP-1 peptide in the range of at least 1 mg, such as at least 5 mg or at least 10 mg. In some embodiments the composition or granule comprises 10 mg GLP-1 peptide.

In some embodiments the composition comprises an amount of a GLP-1 peptide in the range of 0.05 to 25 µmol, such as in the range of 0.5 to 20 µmol.

In some embodiments the GLP-1 peptide is selected from one or more of the GLP-1 peptides mentioned in WO93/19175, WO96/29342, WO98/08871, WO99/43707, WO99/43706, WO99/43341, WO99/43708, WO2005/027978, WO2005/058954, WO2005/058958, WO2006/005667, WO2006/037810, WO2006/037811, WO2006/097537, WO2006/097538, WO2008/023050, WO2009/030738, WO2009/030771 and WO2009/030774.

In some embodiments the GLP-1 peptide is selected from the group consisting of N-epsilon37{2-[2-(2-{2-[2-((R)-3-carboxy-3-{[1-(19-carboxynonadecanoyl) piperidine-4-carbonyl]amino}propionylamino)ethoxy]ethoxy}acetylamino) ethoxy]ethoxy}acetyl [desaminoHis7,Glu22,Arg26,Arg34,Lys37]GLP-1(7-37)amide; N-epsilon26{2-[2-(2-{2-[2-((R)-3-carboxy-3-([1-(19-carboxynonadecanoyl) piperidine-4-carbonyl]amino}propionylamino)ethoxy] ethoxy}acetylamino)ethoxy] ethoxy}acetyl [desaminoHis7,Arg34] GLP-1-(7-37); N-epsilon37{2-[2-(2-{2-[2-((S)-3-carboxy-3-{[1-(19-carboxy-nonadecanoyl) piperidine-4-carbonyl]amino}propionylamino)ethoxy] ethoxy} acetylamino)ethoxy]ethoxy}acetyl[Aib8,Glu22,Arg26,Arg34, Lys37]GLP-1-(7-37)amide; N-epsilon37-[2-(2-[2-(2-[2-(2-((R)-3-[1-(17-carboxyheptadecanoyl)piperidin-4-ylcarbonylamino]3-carboxypropionylamino)ethoxy)ethoxy] acetylamino)ethoxy] ethoxy)acetyl][,DesaminoHis7, Glu22 Arg26, Arg 34, Phe(m-CF3)28]GLP-1-(7-37)amide; N-epsilon26-[(S)-4-carboxy-4-({trans-4-[(19-carboxynonadecanoylamino)methyl]cyclohexanecarbonyl}amino)butyryl] [Aib8,Arg34]GLP-1-(7-37); N-epsilon26-{4-[(S)-4-carboxy-4-({trans-4-[(19-carboxynonadecanoylamino) methyl]cyclohexanecarbonyl}amino)butyrylamino]butyryl}[Aib8,Arg34]GLP-1-(7-37); N-epsilon26-[2-(2-{2-[(S)-4-carboxy-4-({trans-4-[(19-carboxy-nonadecanoylamino) methyl]cyclohexanecarbonyl}amino)butyrylamino] ethoxy}ethoxy)acetyl][Aib8,Arg34]GLP-1-(7-37); N-epsilon26-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy) acetyl][Aib8,Arg34]GLP-1-(7-37)amide; N-epsilon37-[2-(2-{2-[2-(2-{2-[(S)-4-carboxy-4-({trans-4-[(19-carboxy-nonadecanoylamino) methyl]cyclohexanecarbonyl}amino) butyrylamino] ethoxy}ethoxy)acetylamino]ethoxy}ethoxy)acetyl][Aib8, Glu22,Arg26, Arg34,Lys37]GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy}ethoxy)acetyl][DesaminoHis7,Arg26,Arg34,L ys37]GLP-1-(7-37) amide; N-epsilon37-[2-(2-{2-[2-(2-{2-[(S)-4-carboxy-4-({trans-4-[(19-carboxy-nonadecanoylamino)methyl] cyclohexanecarbonyl}amino) butyrylamino]ethoxy}ethoxy) acetylamino]ethoxy}ethoxy)acetyl][DesaminoHis7,Glu22, Arg26,A rg34,Lys37]GLP-1-(7-37); N-epsilon26[2-(2-{2-[2-(2-{2-[(S)-4-carboxy-4-({4-[(19-carboxy-nonadecanoylamino)methyl]cyclohexanecarbonyl}amino) butyrylamino] ethoxy}ethoxy) acetylamino]ethoxy}ethoxy) acetyl[Aib8, Lys 26]GLP-1 (7-37)am ide; N-epsilon26 [2-(2-[2-(2-[2-(2-((S)-2-[trans-4-((9-carboxynonadecanoylamino] methyl) cyclohexylcarbonylamino]-4-carboxybutanoylamino) ethoxy)ethoxy]acetylamino) ethoxy]ethoxy)acetyl][Aib8, Lys26] GLP-1 (7-37)amide; N-epsilon37-[2-(2-{2-[2-(2-{2-[(S)-4-carboxy-4-({trans-4-[(19-carboxy-nonadecanoylamino)methyl]cyclohexane-carbonyl}amino)butyrylamino]ethoxy}ethoxy)acetylamino]ethoxy}ethoxy)acetyl] [DesaminoHis7,Arg26,Arg34,Lys37]GLP-1-(7-37); N-epsilon37-[2-(2-{2-[2-(2-{2-[(S)-4-carboxy-4-({trans-4-[(19-carboxy-nonadecanoylamino)methyl] cyclohexanecarbonyl}amino)butyrylamino]ethoxy}ethoxy) acetylamino]ethoxy}ethoxy)acetyl][DesaminoHis7,Glu22, Arg26,Glu30,Arg34,Lys37]GLP-1-(7-37); N-epsilon26-[2-(2-{2-[(S)-4-carboxy-4-((S)-4-carboxy-4-{4-[4-(16-(1H-tetrazol-5-yl)-hexadecanoylsulfamoyl)butyrylamino]-butyrylamino}butyrylamino) butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino] dodecanoylamino}butyrylamino) butyrylamino] ethoxy}ethoxy)acetyl][Aib8,Arg34]GLP-1-(7-37); N-epsilon26-[2-(2-{2-[(S)-4-carboxy-4-((S)-4-carboxy-4-{6-[4-(16-(1H-tetrazol-5-yl)hexadecanoyl-sulfamoyl)butyrylamino]hexanoylamino} butyrylamino)butyrylamino] ethoxy}ethoxy) acetyl][Aib8,Arg34]GLP-1-(7-37); N-epsilon26-[2-(2-{2-[(S)-4-carboxy-4-((S)-4-carboxy-4-{4-[4-(16-(1H-tetrazol-5-yl)hexadecanoylsulfamoyl)butyrylamino]butyrylamino}butyrylamino)butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino] ethoxy}ethoxy)acetyl][Aib8,Arg34]GLP-1-(7-34); N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-34); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino} butyrylamino)butyrylamino] ethoxy}ethoxy)acetyl][Aib8,Arg34]GLP-1-(7-35); N-epsilon26-[2-(2-{2-[(S)-4-carboxy-4-((S)-4-carboxy-4-{6-[4-(16-(1H-tetrazol-5-yl)hexadecanoylsulfamoyl)butyrylamino]hexanoylamino}butyrylamino)butyrylamino] ethoxy}ethoxy)acetyl][Aib8,Arg34]GLP-1-(7-36)amide; N-epsilon26-[2-(2-{2-[(S)-4-carboxy-4-((S)-4-carboxy-4-{6-[4-(16-(1H-tetrazol-5-yl)hexadecanoylsulfamoyl) butyrylamino]hexanoylamino}butyrylamino) butyrylamino]ethoxy}ethoxy)acetyl][Aib8,Arg34]GLP-1-(7-35); N-epsilon26-[2-(2-{2-[(S)-4-carboxy-4-((S)-4-carboxy-4-{12-[4-(16-(1H-tetrazol-5-yl)hexadecanoyl-sulfamoyl)butyrylamino]dodecanoylamino}butyryl-amino)butyrylamino]ethoxy}ethoxy)acetyl][Aib8,Lys33,Arg34]GLP-1-

(7-34); N-epsilon26-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino)butyrylamino]ethoxy}ethoxy)acetyl][Aib8,Arg34]GLP-1-(7-36)amide; N-epsilon26-[2-(2-{2-[2-(2-{2-[2-(2-{2-[2-(2-{2-[2-(2-{2-[2-(2-{2-[(S)-4-carboxy-4-((S)-4-carboxy-4-{12-[4-(16-(1H-tetrazol-5-yl)hexadecanoylsulfamoyl) butyrylamino]dodecanoylamino}butyrylamino) butyrylamino]ethoxy}ethoxy) acetylamino]ethoxy}ethoxy)acetylamino]ethoxy}ethoxy)acetylamino]ethoxy}ethoxy)acetylamino]ethoxy}ethoxy)acetyl][Aib8,Lys26,Arg34]GLP-1-(7-36)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino]ethoxy}ethoxy)acetyl][Aib8,Glu22,Arg26,Arg34,Lys37]GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl)butyrylamino]dodecanoylamino}butyrylamino) butyrylamino]ethoxy}ethoxy)acetyl][DesaminoHis7,Glu22,Arg26,Arg34,Lys37]GLP-1-(7-37)amide; N-epsilon37{2-[2-(2-{2-[2-((R)-3-carboxy-3-{[1-(19-carboxy-nonadecanoyl) piperidine-4-carbonyl]amino}propionylamino)ethoxy] ethoxy} acetylamino)ethoxy] ethoxy}acetyl [desaminoHis7,Glu22,Arg26,Arg34,Lys37]GLP-1(7-37)amide; N-epsilon37{2-[2-(2-{2-[2-((S)-3-carboxy-3-{[1-(19-carboxynonadecanoyl) piperidine-4-carbonyl]amino}propionylamino) ethoxy]ethoxy}acetylamino)ethoxy] ethoxy} acetyl [Aib8,Glu22,Arg26, Arg34, Lys37]GLP-1-(7-37)amide; N-epsilon37-[2-(2-[2-(2-[2-(2-((R)-3-[1-(17-carboxyhepta-decanoyl)piperidin-4-ylcarbonylamino]3-carboxy-propionylamino) ethoxy)ethoxy] acetylamino) ethoxy]ethoxy)acetyl] [DesaminoHis7, Glu22,Arg26, Arg34,Phe(m-CF3)28] GLP-1-(7-37)amide; N-epsilon37-[2-(2-{2-[2-(2-{2-[(S)-4-carboxy-4-({trans-4-[(19-carboxy-nonadecanoylamino)methyl] cyclohexanecarbonyl} amino)butyrylamino]ethoxy}ethoxy)acetylamino] ethoxy}ethoxy)acetyl] [Aib8,Glu22,Arg26,Arg34,Lys37]GLP-1-(7-37) amide; N-epsilon37-[2-(2-{2-[2-(2-{2-[(S)-4-carboxy-4-({trans-4-[(19-carboxy-nonadecanoylamino)methyl]cyclohexane-carbonyl} amino)butyrylamino]ethoxy}ethoxy)acetylamino]ethoxy}ethoxy)acetyl] [DesaminoHis7,Glu22,Arg26,Arg34,Lys37]GLP-1-(7-37) amide; N-epsilon37-[2-(2-{2-[2-(2-{2-[(S)-4-carboxy-4-({trans-4-[(19-carboxy-nonadecanoylamino) methyl]cyclohexane-carbonyl}amino)butyrylamino]ethoxy}ethoxy) acetylamino]ethoxy}ethoxy) acetyl] [DesaminoHis7,Glu22,Arg26,Arg34,Glu30,Arg34, Lys37] GLP-1-(7-37); N-epsilon37-[2-(2-{2-[(S)-4-carboxy-4-((S)-4-carboxy-4-{12-[4-(16-(1H-tetrazol-5-yl)hexadecanoylsulfamoyl) butyrylamino]dodecanoylamino} butyrylamino) butyrylamino]ethoxy}ethoxy)acetyl] [Aib8,Glu22,Arg26,Arg34,Lys37]GLP-1-(7-37)amide; N-epsilon37-[2-(2-{2-[(S)-4-carboxy-4-((S)-4-carboxy-4-{12-[4-(16-(1H-tetrazol-5-yl)hexadecanoylsulfamoyl) butyrylamino]dodecanoylamino} butyrylamino) butyrylamino]ethoxy}ethoxy)acetyl][DesaminoHis7,Glu22,Arg26,Arg34,Lys37]GLP-1-(7-37)amide; N-epsilon37-(3-((2-(2-(2-(2-(2-Hexadecyloxyethoxy)ethoxy)ethoxy) ethoxy) ethoxy)) propionyl)[DesaminoHis7,Glu22,Arg26,Arg34,Lys37]GLP-1 (7-37)-amide; N-epsilon37-{2-[2-(2-(2-[2-(2-(4-(hexadecanoylamino)-4-carboxybutyryl-amino)ethoxy)ethoxy]acetyl)ethoxy)ethoxy)acetyl)}-[desaminoHis7, Glu22,Arg26, Glu30,Arg34,Lys37] GLP-1-(7-37)amide; N-epsilon37-{2-(2-(2-(2-[2-(2-(4-(hexadecanoylamino)-4-carboxy-butyryl-amino) ethoxy)ethoxy]acetyl)ethoxy) ethoxy) acetyl)}-[desaminoHis7,Glu22, Arg26, Arg34, Lys37]GLP-1-(7-37)amide; N-epsilon37-(2-(2-(2-(2-(2-(2-(2-(2-(octadecanoyl-amino)ethoxy)ethoxy) acetylamino) ethoxy) ethoxy)acetylamino) ethoxy)ethoxy) acetyl)[desaminoHis7,Glu22,Arg26,Arg34,Lys37] GLP-1 (7-37) amide; N-epsilon37-[4-(16-(1H-Tetrazol-5-yl) hexadecanoylsulfamoyl) butyryl] [DesaminoHis7,Glu22, Arg26, Arg34, Lys37]GLP-1-(7-37)amide; N-epsilon37-[2-(2-{2-[2-(2-{2-[(S)-4-carboxy-4-(19-carboxynonadecanoylamino) butyrylamino] ethoxy}ethoxy) acetylamino]ethoxy}ethoxy)acetyl] [DesaminoHis7,Glu22, Arg26, Arg34,Lys37]GLP-1-(7-37); N-epsilon37-(2-{2-[2-((S)-4-carboxy-4-{(S)-4-carboxy-4-[(S)-4-carboxy-4-(19-carboxy-nonadecanoylamino)butyrylamino]butyrylam ino} butyrylamino)ethoxy]ethoxy}acetyl)[DesaminoHis7,Glu22, Arg26,Arg34,Lys37]GLP-1-(7-37); N-epsilon37-{2-[2-(2-{(S)-4-[(S)-4-(12-{4-[16-(2-tert-Butyl-2H-tetrazol-5-yl)-hexadecanoylsulfamoyl]butyrylamino}dodecanoylamino)-4-carboxybutyrylamino]-4-carboxybutyrylamino) ethoxy]acetyl}[DesaminoHis7,Glu22,Arg26,Arg34,Lys37] GLP-1 (7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22, Arg26,Arg34,Lys37]GLP-1-(7-37); N-alpha37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [Aib8,Glu22,Arg26,Arg34,epsilon-Lys37]GLP-1-(7-37)peptide; N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl] [desaminoHis7,Glu22,Arg26,Arg34,Lys37] GLP-1-(7-37); N-epsilon36-[2-(2-{2-[2-(2-{2-[(S)-4-carboxy-4-(15-carboxy-pentadecanoylamino)-butyrylamino]-ethoxy}-ethoxy)-acetylamino]-ethoxy}-ethoxy)- acetyl] [desaminoHis7, Glu22, Arg26,Glu30,Arg34,Lys36] GLP-1-(7-37)-Glu-Lys peptide; N-epsilon37-[2-(2-{2-[2-(2-(2-[(S)-4-carboxy-4-({trans-4-[(19-carboxynonadecanoylamino)methyl] cyclohexanecarbonyl}amino)butyryl-amino] ethoxy}ethoxy)acetylamino]ethoxy}ethoxy)acetyl][Aib8, Glu22,Arg26,Arg34,Lys37]GLP-1-(7-37); N-epsilon37-[2-(2-{2-[2-(2-{2-[(S)-4-carboxy-4-(17-carboxy-heptadecanoylamino)-butyrylamino]-ethoxy}-ethoxy)-acetylamino]-ethoxy}-ethoxy)-acetyl]-[Aib8,Glu22, Arg26, Arg34,Aib35,Lys37]GLP-1-(7-37); N-epsilon37-[(S)-4-carboxy-4-(2-{2-[2-(2-{2-[2-(17-carboxyheptadecanoylamino) ethoxy] ethoxy} acetylamino) ethoxy] ethoxy} acetylamino) butyryl] [Aib8,Glu22,Arg26, 34,Lys37] GLP-1 (7-37); N-epsilon37-[2-(2-[2-(2-[2-(2-[4-(17-carboxyheptadecanoylamino)- 4(S)-carboxybutyrylamino]ethoxy)ethoxy]acetylamino)ethoxy]ethoxy)acetyl] [ImPr7,Glu22, Arg26,34,Lys37], GLP-1-(7-37); N-epsilon26-{2-[2-(2-{2-[2-(2-{(S)-4-carboxy-4-[10-(4-carboxy-phenoxy) decanoylamino]butyrylamino}ethoxy)ethoxy] acetylamino}ethoxy) ethoxy]acetyl}, N-epsilon37-{2-[2-(2-{2-[2-(2-{(S)-4-carboxy-4-[10-(4-carboxy-phenoxy) decanoylamino]butyrylamino}ethoxy)ethoxy] acetylamino}ethoxy) ethoxy]acetyl}-[Aib8,Arg34,Lys37] GLP-1(7-37)-OH; N-epsilon26 (17-carboxyhepta-decanoyl)-[Aib8,Arg34]GLP-1-(7-37)-peptide; N-epsilon26-(19-carboxynonadecanoyl)-[Aib8,Arg34]GLP-1-(7-37); N-epsilon26-(4-{[N-(2-carboxyethyl)-N-(15-carboxypentadecanoyl)amino]methyl}benzoyl[Arg34]GLP-1-(7-37); N-epsilon26-[2-(2-[2-(2-[2-(2-[4-(17-carboxyheptade-canoylamino)-4(S)-carboxybutyrylamino]ethoxy)ethoxy] acetylamino) ethoxy]ethoxy)acetyl][Aib8,Arg34]GLP-1-(7-37); N-epsilon26-[2-(2-[2-(2-[2-(2-[4-(19-carboxynonade-canoylamino)-4(S)-carboxybutyrylamino]ethoxy)ethoxy] acetylamino)ethoxy]ethoxy)acetyl][Aib8,Arg34]GLP-1-(7-37); N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl][3-(4-Imidazolyl)Pro-pionyl7,Arg34]GLP-1-(7-37); N-epsilon26-[2-(2-[2-(2-[2-(2-[4-(17-carboxyheptadecanoylamino)-(carboxymethyl-amino)acetylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-3(S)-Sulfopropionylamino]ethoxy)ethoxy]acetylamino)ethoxy] ethoxy)acetyl][Aib8,Arg34]GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Gly8,Arg34] GLP-1-(7-37); N-epsilon26-[2-(2-[2-(2-[2-(2-[4-(17-carboxyheptadecanoylamino)-4(S)-carboxybutyrylamino]ethoxy)ethoxy]acetylamino)ethoxy] ethoxy)acetyl][Aib8,Arg34]GLP-1-(7-37)-amide; N-epsilon26-[2-(2-[2-(2-[2-(2-[4-(17-carboxyheptade-canoylamino)-4(S)-carboxybutyrylamino]ethoxy)ethoxy] acetylamino)ethoxy]ethoxy)acetyl][Aib8,Arg34,Pro37] GLP-1-(7-37)amide; Aib8,Lys26(N-epsilon26-{2-(2-(2-(2-[2-(2-(4-(pentadecanoylamino)-4-carboxybutyrylamino) ethoxy)ethoxy]acetyl)ethoxy) ethoxy)acetyl)}), Arg34) GLP-1H(7-37)-OH; N-epsilon26-[2-(2-[2-(2-[2-(2-[4-{[N-(2-carboxyethyl)-N-(17-carboxyheptadecanoyl)amino] methyl}benzoyl)amino]ethoxy) ethoxy]acetylamino) ethoxy]ethoxy)acetyl][Aib8,Arg34]GLP-1(7-37); N-alpha7-formyl, N-epsilon26-[2-(2-[2-(2-[2-(2-[4-(17-car-boxyheptadecanoyl-amino)-4(S)-carboxybutyrylamino] ethoxy)ethoxy]acetylamino)ethoxy]ethoxy)acetyl] [Arg34] GLP-1-(7-37); N-epsilon2626-[2-(2-[2-(2-[2-(2-[4-(17-carboxyheptadecanoylamino)-4(S)-carboxybutyrylamino] ethoxy)ethoxy]acetylamino)ethoxy]ethoxy)acetyl][Aib8, Glu22, Arg34] GLP-1-(7-37); N-epsilon26{3-[2-(2-{2-[2-(2-{2-[2-(2-[4-(15-(N—((S)-1,3-dicarboxypropyl) carbam-oyl)pentadecanoylamino)-(S)-4-carboxybutyrylamino] ethoxy)ethoxy]ethoxy}ethoxy)ethoxy]ethoxy}ethoxy) ethoxy]propionyl} [Aib8,Arg34]GLP-1-(7-37); N-epsi-lon26-[2-(2-[2-(2-[2-(2-[4-{[N-(2-carboxyethyl)-N-(17-car-boxy-heptadecanoyl)amino]methyl}benzoyl)amino](4(S)-carboxybutyryl-amino)ethoxy) ethoxy]acetylamino)ethoxy] ethoxy)acetyl][Aib8,Arg34] GLP-1(7-37); N-epsilon26-{ (S)-4-carboxy-4-((S)-4-carboxy-4-((S)-4-carboxy-4-((S)-4-carboxy-4-(19-carboxy-nonadecanoylamino)butyrylamino) butyrylamino)butyrylamino) butyrylamino}[Aib8,Arg34] GLP-1-(7-37); N-epsilon26-4-(17-carboxyheptadecanoyl-amino)-4(S)-carboxybutyryl-[Aib8,Arg34]GLP-1-(7-37); N-epsilon26-{3-[2-(2-{2-[2-(2-{2-[2-(2-[4-(17-carboxy-heptadecanoylamino)-4(S)-carboxybutyrylamino]ethoxy) ethoxy]ethoxy}ethoxy)ethoxy]ethoxy}ethoxy)ethoxy]pro-pionyl}[Aib8,Arg34]GLP-1-(7-37); N-epsilon26-{2-(2-(2-(2-[2-(2-(4-(17-carboxyheptadecanoylamino)-4-carboxybutyrylamino) ethoxy)ethoxy]acetypethoxy)ethoxy) acetyl)}4Aib8,22,27,30,35,Arg34,Pro37, Lys26] GLP-1 (7-37)amide; N-epsilon26-[2-(2-[2-[4-(21-carboxyuneico-sanoylamino)-4(S)-carboxybutyrylamino]ethoxy]ethoxy) acetyl][Aib8,Arg34]GLP-1-(7-37); and N-epsilon26-[2-(2-[2-(2-[2-(2-[4-(21-carboxyuneicosanoylamino)-4(S)-carboxybutyrylamino]ethoxy)ethoxy]acetylamino)ethoxy] ethoxy)acetyl][Aib8,Arg34]GLP-1-(7-37). In one embodiment the GLP-1 peptide is N-epsilon26-{2-[2-(2-{2-[2-(2-{(S)-4-carboxy-4-[10-(4-carboxyphenoxy) decanoy-lamino]butyrylamino}ethoxy)ethoxy] acetylamino}ethoxy) ethoxy]acetyl}, N-epsilon37-{2-[2-(2-{2-[2-(2-{(S)-4-car-boxy-4-[10-(4-carboxy-phenoxy) decanoylamino] butyrylamino}ethoxy)ethoxy]acetylamino}ethoxy) ethoxy] acetyl}-[Aib8,Arg34,Lys37]GLP-1(7-37)-OH (Compound A).

In one embodiment the GLP-1 peptide is N-epsilon26-[2-(2-{2-[2-(2-{2-[(S)-4-carboxy-4-(17-carboxyheptade-canoylamino) butyrylamino]ethoxy}ethoxy)acetylamino] ethoxy}ethoxy)acetyl][Aib8,Arg34]GLP-1(7-37), also known as semaglutide.

In one embodiment GLP-1 peptides can be produced by appropriate derivatisation of an appropriate peptide back-bone which has been produced by recombinant DNA tech-nology or by peptide synthesis (e.g., Merrifield-type solid phase synthesis) as known in the art of peptide synthesis and peptide chemistry.

In one embodiment the production of peptides like GLP-1(7-37) and GLP-1 analogues is well known in the art. The GLP-1 moiety of the GLP-1 peptide of the invention (or fragments thereof) may for instance be produced by classical peptide synthesis, e.g., solid phase peptide synthesis using t-Boc or Fmoc chemistry or other well established tech-niques, see, e.g., Greene and Wuts, "Protective Groups in Organic Synthesis", John Wiley & Sons, 1999, Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

In one embodiment GLP-1 peptides may be produced by recombinant methods, viz. by culturing a host cell contain-ing a DNA sequence encoding the GLP-1 peptide and capable of expressing the peptide in a suitable nutrient medium under conditions permitting the expression of the peptide. Non-limiting examples of host cells suitable for expression of these peptides are: *Escherichia coli, Saccha-romyces cerevisiae*, as well as mammalian BHK or CHO cell lines.

In one embodiment GLP-1 peptides of the invention which include non-natural amino acids and/or a covalently attached N-terminal mono- or dipeptide mimetic may e.g. be produced as described in the experimental part. Or see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Salt of N-(8-(2-hydroxybenzoyl)amino)caprylic acid

The delivery agent used in the present invention is a salt of N-(8-(2-hydroxybenzoyl)amino)caprylic acid. In some embodiments the delivery agent is an absorption enhancer. The structural formula of N-(8-(2-hydroxybenzoyl)amino) caprylate is shown in formula (I).

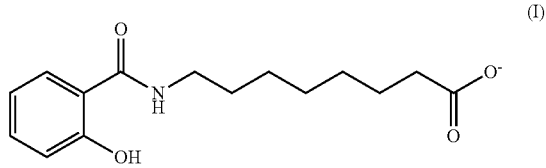 [SMILES: O=C([O-])CCCCCCCNC(=O)c1ccccc1O]

In some embodiments the salt of N-(8-(2-hydroxybenzoyl)amino)caprylic acid is in the caprylic acid form and/or the capraylate form. In some embodiments the salt of N-(8-(2-hydroxybenzoyl)amino)caprylic acid comprises one monovalent cation, two monovalent cations or one divalent cation. In some embodiments the salt of N-(8-(2-hydroxybenzoyl)amino)caprylic acid is selected from the group consisting of the sodium salt, potassium salt and calcium salt of N-(8-(2-hydroxybenzoyl)amino)caprylic acid.

Salts of N-(8-(2-hydroxybenzoyl)amino)caprylate may be prepared using the method described in e.g. WO96/030036, WO00/046182, WO01/092206 or WO2008/028859.

The salt of N-(8-(2-hydroxybenzoyl)amino)caprylic acid may be crystalline and/or amorphous. In some embodiments the delivery agent comprises the anhydrate, monohydrate, dihydrate, trihydrate, a solvate or one third of a hydrate of the salt of N-(8-(2-hydroxybenzoyl)amino) caprylic acid as well as combinations thereof. In some embodiments the delivery agent is a salt of N-(8-(2-hydroxybenzoyl)amino) caprylic acid as described in WO2007/121318. The salt of N-(8-(2-hydroxybenzoyl)amino)caprylic acid may be any polymorph thereof.

In some embodiments the delivery agent is sodium N-(8-(2-hydroxybenzoyl)amino)caprylate (referred to as "SNAC" herein), also known as sodium 8-(salicyloylamino) octanoate.

In some embodiments the amount of the salt of N-(8-(2-hydroxybenzoyl) amino)caprylic acid in the composition is in the range of 0.6-3.5 mmol. In some embodiments the amount of the salt of N-(8-(2-hydroxybenzoyl) amino) caprylic acid in the composition is at least 0.6 mmol, such as selected from the group at least 0.8 mmol or at least 0.9 mmol. In some embodiments the amount of the salt of N-(8-(2-hydroxybenzoyl)amino)caprylic acid in the composition is up to 2.5 mmol. In some embodiments the amount of the salt of N-(8-(2-hydroxybenzoyl)amino)caprylic acid in the composition is 0.6-2.0 mmol. In some embodiments the amount of the salt of N-(8-(2-hydroxybenzoyl)amino) caprylic acid is 1 mmol, such as 1.08 mmol.

In some embodiments the amount of SNAC in the composition is in the range of 100-1000 mg. In some embodiments the amount of SNAC in the composition is at least 150 mg or at least 250 mg. In some embodiments the amount of SNAC in the composition is up to 800 mg, such as up to 700 mg or up to 600 mg. In some embodiments the amount of SNAC in the composition is 300 mg.

In some embodiments the molar ratio between GLP-1 agonist (i.e. GLP-1 peptide) and delivery agent in the composition is less than 10, such as less than 5 or less than 1. In some embodiments the molar ratio between GLP-1 agonist (i.e. GLP-1 peptide) and delivery agent in the composition is less than 1/10, such as less than 1/100 or less than 5/1000.

Pharmaceutical Indications

The present invention also relates to a composition or a granule of the invention for use as a medicament. In one embodiment the composition or the granule is administered orally.

In particular embodiments, the composition or a granule of the invention may be used for the following medical treatments, all preferably relating one way or the other to diabetes:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; and/or delaying gastric emptying;

(vi) prevention and/or treatment of diabetic complications, such as neuropathy, including peripheral neuropathy; nephropathy; or retinopathy;

(vii) improving lipid parameters, such as prevention and/or treatment of dyslipidemia, lowering total serum lipids; lowering HDL; lowering small, dense LDL; lowering VLDL: lowering triglycerides; lowering cholesterol; increasing HDL; lowering plasma levels of lipoprotein a (Lp(a)) in a human; inhibiting generation of apolipoprotein a (apo(a)) in vitro and/or in vivo;

(iix) prevention and/or treatment of cardiovascular diseases, such as syndrome X; atherosclerosis; myocardial infarction; coronary heart disease; stroke, cerebral ischemia; an early cardiac or early cardiovascular disease, such as left ventricular hypertrophy; coronary artery disease; essential hypertension; acute hypertensive emergency; cardiomyopathy; heart insufficiency; exercise tolerance; chronic heart failure; arrhythmia; cardiac dysrhythmia; syncopy; atheroschlerosis; mild chronic heart failure; angina pectoris; cardiac bypass reocclusion; intermittent claudication (atheroschlerosis oblitterens); diastolic dysfunction; and/or systolic dysfunction;

(ix) prevention and/or treatment of gastrointestinal diseases, such as inflammatory bowel syndrome; small bowel syndrome, or Crohn's disease; dyspepsia; and/or gastric ulcers;

(x) prevention and/or treatment of critical illness, such as treatment of a critically ill patient, a critical illness polynephropathy (CIPNP) patient, and/or a potential CIPNP patient; prevention of critical illness or development of CIPNP; prevention, treatment and/or cure of systemic inflammatory response syndrome (SIRS) in a patient; and/or for the prevention or reduction of the likelihood of a patient suffering from bacteraemia, septicaemia, and/or septic shock during hospitalisation; and/or (xi) prevention and/or treatment of polycystic ovary syndrome (PCOS).

In a particular embodiment, the indication is selected from the group consisting of (i)-(iii) and (v)-(iix), such as indications (i), (ii), and/or (iii); or indication (v), indication (vi), indication (vii), and/or indication (iix).

In another particular embodiment, the indication is (i). In a further particular embodiment the indication is (v). In a still further particular embodiment the indication is (iix).

In one embodiment the invention relates to a composition or a granule of the invention for treatment of diabetes or obesity, wherein said granule is administered orally. In one embodiment the invention relates to a method for treatment of diabetes or obesity comprising oral administration of a composition comprising a composition or a granule of the invention to a patient in need thereof.

The following indications are particularly preferred: Type 2 diabetes, and/or obesity.

Particular Embodiments

The following are particular embodiments of the invention
1. A pharmaceutical composition comprising a first type and a second type of granules, wherein said first type of granules comprises a salt of N-(8-(2-hydroxybenzoyl)amino)caprylic acid, and wherein said second type of granules comprises a GLP-1 peptide.
2. A pharmaceutical composition according to any one of the preceding embodiments, wherein said first type of granules does not comprise GLP-1 peptide.
3. A pharmaceutical composition according to any one of the preceding embodiments, wherein said second type of granules does not comprise salt of N-(8-(2-hydroxybenzoyl)amino)caprylic acid.
4. A pharmaceutical composition according to any one of the preceding embodiments, wherein said first type of granules further comprises a lubricant, such as magnesium stearate.
5. A pharmaceutical composition according to any one of the preceding embodiments, wherein said first type of granules further comprises a filler, such as microcrystalline cellulose.
6. A pharmaceutical composition according to any one of the preceding embodiments, wherein said second type of granules further comprises a filler, such as microcrystalline cellulose.
7. A pharmaceutical composition according to any one of the preceding embodiments, wherein said second type of granules further comprises a binder, such as povidone.
8. A pharmaceutical composition according to any one of the preceding embodiments, wherein the granules are manufactured by dry granulation, such as by roller compaction.
9. A pharmaceutical composition according to any one of the preceding embodiments, wherein the release of said salt of N-(8-(2-hydroxybenzoyl)amino)caprylic acid is simultaneous with or faster than the release of said GLP-1 peptide.
10. A pharmaceutical composition according to any one of the preceding embodiments, wherein said the release of said salt of N-(8-(2-hydroxybenzoyl)amino)caprylic acid and/or said GLP-1 peptide is determined by dissolution testing using Assay (I) and wherein said release is optionally determined within 30 minutes of said dissolution testing.
11. A pharmaceutical composition comprising a salt of N-(8-(2-hydroxybenzoyl)amino)caprylic acid and a GLP-1 peptide, wherein the release of said salt of N-(8-(2-hydroxybenzoyl)amino)caprylic acid is simultaneous with or faster than the release of said GLP-1 peptide as determined by dissolution testing using Assay (I).
12. A pharmaceutical composition according to any one of the preceding embodiments, wherein the amount of dissolved salt of N-(8-(2-hydroxybenzoyl)amino)caprylic acid peaks within the first 60 minutes as determined by dissolution testing using Assay (I) at pH 2.5.
13. A pharmaceutical composition according to any one of the preceding embodiments, wherein the amount of dissolved salt of N-(8-(2-hydroxybenzoyl)amino)caprylic acid peaks within 55 minutes, such as within 50, 45, 40, 39, 38, 37, 36, 35, 34, 33, 32, or 31 minutes as determined by dissolution testing using Assay (I) at pH 2.5.
14. A pharmaceutical composition according to any one of the preceding embodiments, wherein the amount of dissolved salt of N-(8-(2-hydroxybenzoyl)amino)caprylic acid peaks within the first 30 minutes as determined by dissolution testing using Assay (I) at pH 2.5.
15. A pharmaceutical composition according to any one of the preceding embodiments, wherein the amount of dissolved salt of N-(8-(2-hydroxybenzoyl)amino)caprylic acid peaks within 31 minutes, such as within 32, 33, 34, 35, 36, 37, 38, 39, 40, 45, 50, 55, or 60 minutes as determined by dissolution testing using Assay (I) at pH 2.5.
16. A pharmaceutical composition according to any one of the preceding embodiments, wherein the amount of dissolved salt of N-(8-(2-hydroxybenzoyl)amino)caprylic acid peaks within 30 minutes, such as within 25, 20, 15, 10, or 5 minutes as determined by dissolution testing using Assay (I) at pH 2.5.
17. A pharmaceutical composition according to any one of the preceding embodiments, wherein said dissolution testing using Assay (I) is carried out at any one of pH 1.0-8.0.
18. A pharmaceutical composition according to any one of the preceding embodiments, wherein said dissolution testing using Assay (I) is carried out at pH 1.0.
19. A pharmaceutical composition according to any one of the preceding embodiments, wherein said dissolution testing using Assay (I) is carried out at pH 2.5.
20. A pharmaceutical composition according to any one of the preceding embodiments, wherein said dissolution testing using Assay (I) is carried out at pH 6.8.
21. A pharmaceutical composition according to any one of the preceding embodiments, wherein the salt of N-(8-(2-hydroxybenzoyl)amino)caprylic acid is SNAC.
22. A pharmaceutical composition according to any one of the preceding embodiments, wherein the GLP-1 peptide comprises an albumin binding moiety.
23. A pharmaceutical composition according to any one of the preceding embodiments, wherein the GLP-1 peptide is N-epsilon26-[2-(2-{2-[2-(2-{2-[(S)-4-carboxy-4-(17-carboxyheptadecanoylamino) butyrylamino]ethoxy}ethoxy)acetylamino]ethoxy}ethoxy)acetyl][Aib8,Arg34]GLP-1 (7-37).
24. A pharmaceutical composition according to any one of the preceding embodiments, wherein said composition further comprises one or more pharmaceutically acceptable excipients.
25. A pharmaceutical composition according to any one of the preceding embodiments, wherein said composition is in the form of a solid dosage form.
26. A pharmaceutical composition according to any one of the preceding embodiments, wherein said composition is in the form of a tablet.
27. A pharmaceutical composition according to any one of the preceding embodiments, wherein said composition is in the form of a capsule.
28. A pharmaceutical composition according to any one of the preceding embodiments, wherein said composition is in the form of a sachet.
29. A pharmaceutical composition according to any one of the preceding embodiments further comprising any combination of the features according to embodiments 1-28.

30. A process of producing a pharmaceutical composition comprising a salt of N-(8-(2-hydroxybenzoyl)amino) caprylic acid and a GLP-1 peptide, wherein the process comprises the steps:
    a) mixing a GLP-1 peptide with a filler and/or a binder;
    b) dry granulation of the mixture of step a;
    c) mixing the granules obtained in step b with a composition comprising a salt of N-(8-(2-hydroxybenzoyl) amino)caprylic acid; and
    d) optionally adding further lubricant.

31. A process of producing a pharmaceutical composition comprising a salt of N-(8-(2-hydroxybenzoyl)amino) caprylic acid and a GLP-1 peptide, wherein the process comprises the steps:
    a) mixing a salt of N-(8-(2-hydroxybenzoyl)amino) caprylic acid with a lubricant and/or a filler;
    b) dry granulation of the mixture of step a;
    c) mixing the granules obtained in step b with a composition comprising a GLP-1 peptide; and
    d) optionally adding further lubricant.

32. A process of producing a pharmaceutical composition comprising a salt of N-(8-(2-hydroxybenzoyl)amino) caprylic acid and a GLP-1 peptide, wherein the process comprises the steps:
    a) mixing a GLP-1 peptide with a filler and/or a binder;
    b) dry granulation of the mixture of step a;
    c) mixing a salt of N-(8-(2-hydroxybenzoyl)amino) caprylic acid, optionally a lubricant and/or a filler;
    d) dry granulation of the mixture of step c;
    e) mixing the granules obtained in step b with the granules obtained in step d; and
    f) optionally adding further lubricant.

33. A process according to any one of embodiments 30-32, wherein said dry granulation is roller compaction.

34. A process according to any one of embodiments 30-33, wherein said salt of N-(8-(2-hydroxybenzoyl)amino) caprylic acid is SNAC.

35. A process according to any one of embodiments 30-34, wherein said GLP-1 peptide is semaglutide.

36. A process according to any one of embodiments 30-35, wherein said lubricant and/or said further lubricant is magnesium stearate.

37. A process according to any one of embodiments 30-36, wherein said filler is microcrystalline cellulose.

38. A process according to any one of embodiments 30-37, wherein said binder is povidone.

39. A process according to any one of embodiments 30-38, wherein said mixing step comprising mixing of a salt of N-(8-(2-hydroxybenzoyl)amino)caprylic acid with a lubricant and/or a filler prior to dry granulation has a duration of at least 20 minutes, such as at least 30 minutes or at least 40 minutes, such as 50 minutes.

40. A process according to any one of embodiments 30-39, wherein said mixing comprising mixing of the first type of granules comprising a GLP-1 peptide with the second type of granules comprising a salt of N-(8-(2-hydroxybenzoyl)amino)caprylic acid has a duration of at least 15 minutes or at least 20 minutes, such as 25 minutes or at least 30 minutes.

41. A pharmaceutical composition obtained by the process as defined in any one of embodiments 30-40.

42. A pharmaceutical composition as defined in any one of embodiments 1-29 or 41 for use in medicine.

43. A pharmaceutical composition as defined in any one of embodiments 1-29 or 41 for treatment of diabetes or obesity.

44. A pharmaceutical composition according to embodiment 42 or 43, wherein said pharmaceutical composition is administered orally.

45. A method for treatment of diabetes or obesity comprising administration of a composition comprising the pharmaceutical composition as defined in any one of embodiments 1-29 or 41 to a patient in need thereof.

46. A method according to embodiment 45, wherein said composition is administered orally.

47. A granule comprising a salt of N-(8-(2-hydroxybenzoyl) amino)caprylic acid, a lubricant, and a filler.

48. A granule comprising a salt of N-(8-(2-hydroxybenzoyl) amino)caprylic acid and a lubricant.

49. A granule comprising a GLP-1 peptide, a filler and a binder.

50. A granule according to any one of embodiments 47-49, wherein said lubricant is magnesium stearate.

51. A granule according to any one of embodiments 47-50, wherein said filler is microcrystalline cellulose.

52. A granule according to any one of embodiments 47-51, wherein said binder is povidone.

53. A granule according to any one of embodiments 47-52, wherein said granule is prepared according to the process as defined in any one of embodiments 30-40.

54. A process of producing a granule comprising a salt of N-(8-(2-hydroxybenzoyl)amino)caprylic acid, wherein the process comprises the steps:
    a) mixing a salt of N-(8-(2-hydroxybenzoyl)amino) caprylic acid (such as SNAC) with a lubricant and/or a filler; and
    b) dry granulation of the mixture of step a.

55. A process according to embodiment 54, wherein said salt of N-(8-(2-hydroxybenzoyl)amino)caprylic acid is SNAC.

56. A process according to embodiment 54 or 55, wherein said lubricant is magnesium stearate.

57. A process according to any one of embodiments 54-56, wherein said mixing step comprising mixing of a salt of N-(8-(2-hydroxybenzoyl)amino)caprylic acid with a lubricant and/or a filler prior to dry granulation has a duration of at least 20 minutes, such as at least 30 minutes or at least 40 minutes, such as 50 minutes.

58. A process of producing a granule comprising a GLP-1 peptide, wherein the process comprises the steps:
    a) mixing a GLP-1 peptide, optionally a filler and/or a binder; and
    b) roller compacting the mixture of step a.

59. A process according to embodiment 58, wherein said GLP-1 peptide is semaglutide.

60. A process according to any one of embodiments 58-59, wherein said binder is povidone.

61. A process according to any one of embodiments 58-60, wherein said filler is microcrystalline cellulose.

62. A process according to any one of embodiments 58-61, wherein said dry granulation is roller compaction.

63. A granule obtained by the process as defined in any one of embodiments 58-62.

64. A method for increasing oral bioavailability of a GLP-1 peptide comprising administration to a patient in need thereof of a composition as defined in any of embodiments 1-29 or 41.

65. A pharmaceutical composition according to any one of the preceding embodiments wherein said simultaneous or faster release is determined within 30 minutes, such as within 25, 20, 15 or 10 minutes, as determined by dissolution testing using Assay (I).

66. A pharmaceutical composition according to any one of the preceding embodiments wherein said simultaneous or faster release is determined within 30 minutes, such as within 25, 20, 15 or 10 minutes, as determined by dissolution testing using Assay (I) at pH 2.5.

Further Particular Embodiments

The following are further particular embodiments of the invention:
1. A pharmaceutical composition comprising a salt of N-(8-(2-hydroxybenzoyl)amino)caprylic acid and a GLP-1 peptide, wherein the release of said salt of N-(8-(2-hydroxybenzoyl)amino)caprylic acid is simultaneous with or faster than the release of said GLP-1 peptide as determined by dissolution testing using Assay (I).
2. A pharmaceutical composition according to any one of the preceding embodiments, wherein the amount of dissolved salt of N-(8-(2-hydroxybenzoyl)amino)caprylic acid peaks within the first 30 minutes as determined by dissolution testing using Assay (I) at pH 2.5.
3. A pharmaceutical composition according to any one of the preceding embodiments, wherein the amount of dissolved salt of N-(8-(2-hydroxybenzoyl)amino)caprylic acid peaks within 31 minutes, such as within 32, 33, 34, 35, 36, 37, 38, 39, 40, 45, 50, 55, or 60 minutes as determined by dissolution testing using Assay (I) at pH 2.5.
4. A pharmaceutical composition according to any one of the preceding embodiments, wherein said dissolution testing using Assay (I) is carried out at any one of pH 1.0-8.0.
5. A pharmaceutical composition according to any one of the preceding embodiments, wherein said dissolution testing using Assay (I) is carried out at pH 1.0.
6. A pharmaceutical composition according to any one of the preceding embodiments, wherein said dissolution testing using Assay (I) is carried out at pH 2.5.
7. A pharmaceutical composition according to any one of the preceding embodiments, wherein said dissolution testing using Assay (I) is carried out at pH 6.8.
8. A pharmaceutical composition according to any one of the preceding embodiments, wherein the salt of N-(8-(2-hydroxybenzoyl)amino)caprylic acid is SNAC.
9. A pharmaceutical composition according to any one of the preceding embodiments, wherein the GLP-1 peptide comprises an albumin binding moiety.
10. A pharmaceutical composition according to any one of the preceding embodiments, wherein the GLP-1 peptide is N-epsilon26-[2-(2-{2-[2-(2-{2-[(S)-4-carboxy-4-(17-carboxyheptadecanoylamino) butyrylamino]ethoxy}ethoxy) acetylamino]ethoxy}ethoxy)acetyl][Aib8,Arg34]GLP-1 (7-37).
11. A pharmaceutical composition comprising a first type and a second type of granules, wherein said first type of granules comprises a salt of N-(8-(2-hydroxybenzoyl) amino)caprylic acid and said second type of granules comprises a GLP-1 peptide.
12. A pharmaceutical composition according to embodiment 11, wherein said first type of granules further comprises a lubricant, such as magnesium stearate.
13. A pharmaceutical composition according to embodiment 11 or 12, wherein said first type of granules further comprises a filler, such as microcrystalline cellulose.
14. A pharmaceutical composition according to any one of embodiments 11-13, wherein said second type of granules further comprises a filler, such as microcrystalline cellulose.
15. A pharmaceutical composition according to any one of embodiments 11-14, wherein said second type of granules further comprises a binder, such as povidone.
16. A pharmaceutical composition according to any one of embodiments 11-15, wherein the granules are manufactured by dry granulation, such as by roller compaction.
17. A pharmaceutical composition according to any one of embodiments 11-16 further comprising any combination of the features according to embodiments 1-10.
18. A pharmaceutical composition according to any one of the preceding embodiments, wherein said composition further comprises one or more pharmaceutically acceptable excipients.
19. A pharmaceutical composition according to any one of the preceding embodiments, wherein said composition is in the form of a solid dosage form.
20. A pharmaceutical composition according to any one of the preceding embodiments, wherein said composition is in the form of a tablet.
21. A pharmaceutical composition according to any one of the preceding embodiments, wherein said composition is in the form of a capsule.
22. A pharmaceutical composition according to any one of the preceding embodiments, wherein said composition is in the form of a sachet.
23. A process of producing a pharmaceutical composition comprising a salt of N-(8-(2-hydroxybenzoyl)amino) caprylic acid and a GLP-1 peptide, wherein the process comprises the steps:
 a) mixing a GLP-1 peptide with a filler and/or a binder;
 b) dry granulation of the mixture of step a;
 c) mixing the granules obtained in step b with a composition comprising a salt of N-(8-(2-hydroxybenzoyl) amino)caprylic acid; and
 d) optionally adding further lubricant.
24. A process of producing a pharmaceutical composition comprising a salt of N-(8-(2-hydroxybenzoyl)amino) caprylic acid and a GLP-1 peptide, wherein the process comprises the steps:
 a) mixing a salt of N-(8-(2-hydroxybenzoyl)amino) caprylic acid with a lubricant and/or a filler;
 b) dry granulation of the mixture of step a;
 c) mixing the granules obtained in step b with a composition comprising a GLP-1 peptide; and
 d) optionally adding further lubricant.
25. A process of producing a pharmaceutical composition comprising a salt of N-(8-(2-hydroxybenzoyl)amino) caprylic acid and a GLP-1 peptide, wherein the process comprises the steps:
 a) mixing a GLP-1 peptide with a filler and/or a binder;
 b) dry granulation of the mixture of step a;
 c) mixing a salt of N-(8-(2-hydroxybenzoyl)amino) caprylic acid, optionally a lubricant and/or a filler;
 d) dry granulation of the mixture of step c;
 e) mixing the granules obtained in step b with the granules obtained in step d; and
 f) optionally adding further lubricant.
26. A process according to any one of embodiments 23-25, wherein said dry granulation is roller compaction.
27. A process according to any one of embodiments 23-26, wherein said salt of N-(8-(2-hydroxybenzoyl)amino) caprylic acid is SNAC.
28. A process according to any one of embodiments 23-27, wherein said GLP-1 peptide is semaglutide.
29. A process according to any one of embodiments 23-28, wherein said lubricant and/or said further lubricant is magnesium stearate.

30. A process according to any one of embodiments 23-29, wherein said filler is microcrystalline cellulose.
31. A process according to any one of embodiments 23-30, wherein said binder is povidone.
32. A process according to any one of embodiments 23-31, wherein said mixing step comprising mixing of a salt of N-(8-(2-hydroxybenzoyl)amino)caprylic acid with a lubricant and/or a filler prior to dry granulation has a duration of at least 30 minutes or at least 40 minutes, such as 50 minutes.
33. A process according to any one of embodiments 23-32, wherein said mixing comprising mixing of the first type of granules comprising a GLP-1 peptide with the second type of granules comprising a salt of N-(8-(2-hydroxybenzoyl)amino)caprylic acid has a duration of at least 15 minutes or at least 20 minutes, such as 25 minutes.
34. A pharmaceutical composition obtained by the process as defined in any one of embodiments 23-33.
35. A pharmaceutical composition as defined in any one of embodiments 1-22 or 34 for use in medicine.
36. A pharmaceutical composition as defined in any one of embodiments 1-22 or 34 for treatment of diabetes or obesity.
37. A pharmaceutical composition according to embodiment 35 or 36, wherein said pharmaceutical composition is administered orally.
38. A method for treatment of diabetes or obesity comprising administration of a composition comprising the pharmaceutical composition as defined in any one of embodiments 1-22 or 34 to a patient in need thereof.
39. A method according to embodiment 38, wherein said composition is administered orally.
40. A granule comprising a salt of N-(8-(2-hydroxybenzoyl)amino)caprylic acid, a lubricant, and a filler.
41. A granule comprising a salt of N-(8-(2-hydroxybenzoyl)amino)caprylic acid and a lubricant.
42. A granule comprising a GLP-1 peptide, a filler and a binder.
43. A granule according to any one of embodiments 40-42, wherein said lubricant is magnesium stearate.
44. A granule according to any one of embodiments 40-43, wherein said filler is microcrystalline cellulose.
45. A granule according to any one of embodiments 40-44, wherein said binder is povidone.
46. A granule according to any one of embodiments 40-45, wherein said granule is prepared according to the process as defined in any one of embodiments 23-34.
47. A process of producing a granule comprising a salt of N-(8-(2-hydroxybenzoyl)amino)caprylic acid, wherein the process comprises the steps:
    a) mixing a salt of N-(8-(2-hydroxybenzoyl)amino)caprylic acid (such as SNAC) with a lubricant and/or filler; and
    b) dry granulation of the mixture of step a.
48. A process according to embodiment 47, wherein said salt of N-(8-(2-hydroxybenzoyl)amino)caprylic acid is SNAC.
49. A process according to embodiment 47 or 48, wherein said lubricant is magnesium stearate.
50. A process according to any one of embodiments 47-49, wherein said mixing step comprising mixing of a salt of N-(8-(2-hydroxybenzoyl)amino)caprylic acid with a lubricant and/or a filler prior to dry granulation has a duration of at least 30 minutes or at least 40 minutes, such as 50 minutes.
51. A process of producing a granule comprising a GLP-1 peptide, wherein the process comprises the steps:
    a) mixing a GLP-1 peptide, optionally a filler and/or a binder; and
    b) roller compacting the mixture of step a.
52. A process according to embodiment 51, wherein said GLP-1 peptide is semaglutide.
53. A process according to any one of embodiments 51-52, wherein said binder is povidone.
54. A process according to any one of embodiments 47-53, wherein said filler is microcrystalline cellulose.
55. A process according to any one of embodiments 47-54, wherein said dry granulation is roller compaction.
56. A granule obtained by the process as defined in any one of embodiments 47-55.
57. A granule as defined in any one of embodiments 40-46 or 56 for use in medicine.
58. A granule as defined in any one of embodiments 40-46 or 56 for treatment of diabetes or obesity.
59. A granule according to embodiment 57 or 58, wherein said granule is administered orally in a pharmaceutical composition.
60. A method for treatment of diabetes or obesity comprising oral administration of a pharmaceutical composition comprising the granule as defined in any one of embodiments 40-46 or 56 to a patient in need thereof.
61. A method according to embodiment 60, wherein said pharmaceutical composition is administered orally.

EXAMPLES

Materials and Methods
General Methods of Preparation
Dry Granulation

Dry granulation was carried out by roller compaction on a Gerteis MINI-PACTOR using smooth rolls and the settings listed in Table 1.

TABLE 1

Settings for dry granulation on the roller compactor

| Parameter | Setting |
| --- | --- |
| Agitator speed | 5.0 rpm |
| Roll speed | 1.5 or 3.0 rpm |
| Gap | 1.0 mm |
| Force | 5.0 or 6.0 kN/cm |
| Granulator screen | 0.63 mm wire screen |
| Granulator speed | 60 rpm |

Roller compaction force, i.e. the force between the rolls of the roller compactor when compacting materials into a continuous strip of compressed material, was determined by a pressure transducer that converts the hydraulic pressure into electrical signal; the roller compaction force may be measured in kiloNewton (kN) or in kiloNewton per roll width (kN/cm).

Subsequent to dry granulation comminution of the moldings into granules was carried out.

Tablet Preparation

Tablets were produced on a Korsch PH106 or a Fette 102i mounted with a gravity feeder and a single set of punches resulting in 13 mm×7.5 mm convex oval tablets having no score. The press speed of the Korsch PH106 was set around 25 rpm and the counter pressure was adjusted to 40 kN. The press speed of the Fette 102i was set around 20 rpm. The fill volume was adjusted to obtain tablets having a target weight 407.7 mg. The compression force was set to obtain tablets with a crushing strength of around 180±20 N for the Korsch PH106 and of around 128 N for the Fette 102i.

Resistance to Crushing of Tablets

Resistance to crushing of tablets was determined according to section 2.9.8 in the European Pharmacopoeia 7.5, 7th edition 2012 and at a jaw speed of 20 N/s.

General Methods of Detection and Characterisation

Assay (I): Dissolution Testing

The dissolution test was conducted with apparatus 2 in accordance with United States Pharmacopoeia 35 using a paddle rotation speed of 50 rpm. For testing at pH 1.0, 2.5 or 6.8, the 500 mL dissolution medium of 0.1 N hydrochloric acid (pH 1.0), 0.05 M phthalate buffer (pH 2.5), or 0.05 M phosphate buffer (pH 6.8), respectively, was used at a temperature of 37° C. All dissolution media had a content of 0.1% Tween80. Sample aliquots were removed at appropriate intervals and samples with acidic medium were neutralized with tribasic sodium phosphate to prevent precipitation. Sample contents were determined using a RP-HPLC method for dual detection of SNAC and GLP-1 (e.g. semaglutide) The HPLC method was based on gradient elution on a C8 column. The solvent system was trifluoroacetic acid and acetonitrile with UV detection at 210 and 335 nm. The sample contents were calculated based on the peak area of the SNAC and GLP-1 (e.g. semaglutide) peaks in the chromatogram relative to the peak areas of the SNAC and GLP-1 (e.g. semaglutide) references, respectively. The released amounts of SNAC and GLP-1 (e.g. semaglutide) were calculated as percentages of the nominal contents in the tablet i.e. 300 mg/tablet SNAC and 10 mg/tablet GLP-1 (e.g. semaglutide) and then optionally corrected for the actual contents in the tablets. The actual contents in the tablets were determined using Assay (III).

Assay (II): Bioavailability in Dogs

Animals, Dosing and Blood Sampling: Male and female beagle dogs, weighing approx. 6-22 kg during the study period, were included in the study. The dogs were dosed in fasting state and the dogs were fed approx. 4 hours post dosing. The formulations were administered by oral administration to the dogs in groups of typically 8 (such as 4 male and 4 females).

The bioavailability studies were conducted either as single dose (SD) studies or multiple dose (MD) studies. In the MD studies the formulation was administered with five consecutive dosing occasions in each study (once a day dosing).

Blood samples were taken to cover the pharmacokinetic profile. An example of a SD blood sampling regimen could be the following time points: pre-dose, 0.25, 0.5, 0.75, 1, 1.5, 2, 2.5, 3, 4, 6, 8, 24, 48, 72, 96, 120, 144, 192 and 240 hours post dosing. An example of a MD blood sampling regimen could be the following time points: pre-dose, 0.5, 1.5 and 3 hr post dosing after each dosing occasion and a blood sampling regimen equivalent to a SD blood sampling regimen following the last dosing occasion.

Preparation of Plasma: All blood samples were collected into test tubes containing EDTA for stabilisation and kept on ice until centrifugation. Plasma was separated from whole blood by centrifugation and the plasma was stored at −20° C. or lower until analysis.

Analysis of Plasma Samples: The plasma was analysed for semaglutide using a Luminescence Oxygen Channeling Immunoassay (LOCI). The LOCI assay employs donor beads coated with streptavidin and acceptor beads conjugated with a monoclonal antibody binding to a mid-molecular region of GLP-1 (e.g. semaglutide). The other monoclonal antibody, specific for an N-terminal epitope, was biotinylated. In the assay the three reactants were combined with the GLP-1 (e.g. semaglutide) which form a two-sited immuno-complex. Illumination of the complex releases singlet oxygen atoms from the donor beads which channels into the acceptor beads and trigger chemiluminescence which was measured in the EnVision plate reader. The amount of light was proportional to the concentration of semaglutide and the lower limit of quantification (LLOQ) in plasma was 100 pM.

Pharmacokinetic Calculations: GLP-1 (e.g. semaglutide) plasma concentration data were subjected to non-compartmental pharmacokinetic analysis using the PC based software WinNonlin, v. 5.2 or later (Pharsight, Mountain View, Calif. 94041, USA). For each individual dog the following pharmacokinetic parameters were estimated: Area Under the Curve (AUC), and dose normalized AUC (AUC/D). Bioavailability (F) was calculated as the fraction absorbed (in %) based on the dose normalised AUC (AUCinf./D) following oral and intravenous administration. Summary statistics of pharmacokinetic results were presented as arithmetic mean.

Assay (III): Analysis of Amount of GLP-1 and SNAC

For assay analysis tablets were dissolved using 0.05 M $Na_2HPO_4$ with 0.01% Tween20 as extraction buffer. Sample content was determined using a RP-HPLC method for dual detection of SNAC and GLP-1 (e.g. semaglutide). The HPLC method was based on gradient elution on a C8 column. The solvent system was trifluoroacetic acid and acetonitrile with UV detection at 210 and 335 nm. The sample contents were calculated based on the peak area of the SNAC and GLP-1 (e.g. semaglutide) peaks in the chromatogram relative to the peak areas of the SNAC and GLP-1 (e.g. semaglutide) references, respectively. The content was reported as average of 10 tablets.

Example 1

Preparation of Tablet Compositions Comprising GLP-1 and SNAC

Tablet compositions comprising GLP-1 and SNAC were prepared with the components shown in Table 2. Compound A is N-epsilon26-{2-[2-(2-{2-[2-(2-{(S)-4-carboxy-4-[10-(4-carboxyphenoxy) decanoylamino]butyrylamino}ethoxy) ethoxy] acetylamino}ethoxy) ethoxy]acetyl}, N-epsilon37-{2-[2-(2-{2-[2-(2-{(S)-4-carboxy-4-[10-(4-carboxyphenoxy) decanoylamino] butyrylamino}ethoxy)ethoxy] acetylamino}ethoxy) ethoxy]acetyl}-[Aib8,Arg34,Lys37] GLP-1(7-37)-OH.

TABLE 2

Composition of the tablet compositions

| Component | Amount (mg/tablet) | Function |
|---|---|---|
| Semaglutide or Compound A | 10 | Active ingredient |
| SNAC | 300 | Delivery agent |
| Microcrystalline cellulose (Avicel PH 101) | 80 | Filler |
| Povidone K 90 (Kollidon 90F) | 8 | Binder |
| Magnesium stearate | 9.7 | Lubricant |
| Total amount | 407.7 | |

Tablet compositions were prepared by mixing the components listed in Table 2 in different ways. The tablet compositions consisted of a first type of granules, in some cases a second type of granules, as well as extragranular ingredients mixed with the first type of granules and, if present, the second type of granules. Preparation of granules by roller compaction and preparation of tablets from the tablet compositions were as described in the section General Methods of Preparation. The design of the tablet compositions is shown in Table 3.

TABLE 3

Design of tablet compositions (the amount of each component in mg/tablet is shown in brackets)

| Tablet composition | Composition of first type of granules (mg/tablet) | Composition of second type of granules (mg/tablet) | Extragranular ingredients (mg/tablet) |
|---|---|---|---|
| B | SNAC (300), magnesium stearate (7.7) | semaglutide (10), microcrystalline cellulose (80), povidone (8) | magnesium stearate (2) |
| C | SNAC (300), semaglutide (10), magnesium stearate (7.7) | — | microcrystalline cellulose (80), povidone (8), magnesium stearate (2) |
| D | SNAC (300), semaglutide (10), povidone (8), magnesium stearate (7.7) | — | microcrystalline cellulose (80), magnesium stearate (2) |
| E | SNAC (300), semaglutide (10), microcrystalline cellulose (80), povidone (8), magnesium stearate (7.7) | — | magnesium stearate (2) |
| F | SNAC (300), microcrystalline cellulose (57), magnesium stearate (7.7) | semaglutide (10), microcrystalline cellulose (23), povidone (8) | magnesium stearate (2) |
| G | SNAC (300), magnesium stearate (7.7) | Compound A (10), microcrystalline cellulose (80), povidone (8) | magnesium stearate (2) |
| H | SNAC (300), microcrystalline cellulose (57), magnesium stearate (7.7) | Compound A (10), microcrystalline cellulose (23), povidone (8) | magnesium stearate (2) |

Further details of the preparation of the tablet compositions are provided below.

Tablet Composition B

Magnesium stearate for the first granule fraction was passed through a 355 μm sieve. Magnesium stearate was manually mixed with SNAC in a stainless steel bowl in corresponding volumes. Two cycles of geometric dilution was applied by mixing for around 60 s until the blend was visually homogenous. The remaining quantity of SNAC was transferred to a blender and was pre-mixed for 2 min at 25 rpm. The SNAC and magnesium stearate pre-mix was added to the blender and mixing was performed for 20 min at 25 rpm. The blend was roller compacted. The granules were sieved through a 180 μm mesh.

Semaglutide, microcrystalline cellulose and povidone for the second granule fraction were weighed directly into a stainless steel bowl in the order of decreasing amounts and mixed manually for at least 3 min until visually homogenous before transferring the pre-mix to a 1000 mL Duma bottle. The Duma bottle was closed with a lid and tumbled manually in a Turbula-like movement for 1 min. The blend was roller compacted.

The two types of granules were added to a blending container in order of decreasing content and mixed for 5 minutes at 32 rpm. Extragranular magnesium stearate was mixed with the granule blend by manual mixing using volume-doubling followed by 30 s mixing in the Turbula mixer at 32 rpm. Tablets were prepared from this composition.

Tablet Composition C

Magnesium stearate for the granule fraction was passed through a 355 μm sieve. Magnesium stearate was manually mixed with SNAC in a stainless steel bowl in corresponding volumes. Two cycles of geometric dilution was applied by mixing for around 60 s until the blend was visually homogenous. The remaining quantity of SNAC was transferred to a blender and was pre-mixed for 2 min at 25 rpm. The SNAC and magnesium stearate pre-mix was added to the blender and mixing was performed for 20 min at 25 rpm. Semaglutide was geometrically diluted using the mixed SNAC and magnesium stearate from the blender by mixing it manually for at least 60 s until visually homogenous. The pre-mix was then added to the mixed SNAC and magnesium stearate. The mixing step was finalized by mixing in the blender for 10 min at 25 rpm. The blend was roller compacted.

The granules and all other constituents except extragranular magnesium stearate were added to a blending container in order of decreasing content and mixed for 5 minutes at 32 rpm. Extragranular magnesium stearate was mixed with the granule blend by manual mixing using volume-doubling followed by 30 s mixing in the Turbula mixer at 32 rpm. Tablets were prepared from this composition.

Tablet Composition D

Magnesium stearate for the granule fraction was passed through a 355 μm sieve. Magnesium stearate was manually mixed with SNAC in a stainless steel bowl in corresponding volumes. Two cycles of geometric dilution was applied by mixing for around 60 s until the blend was visually homogenous. The remaining quantity of SNAC was transferred to a blender and was pre-mixed for 2 min at 25 rpm. The SNAC and magnesium stearate pre-mix was added to the blender and mixing was performed for 20 min at 25 rpm. Semaglutide and povidone were weighed into a stainless steel bowl in the order of decreasing amounts and the components were mixed manually until visually homogenous. A geometric dilution was then performed using the mixed SNAC and magnesium stearate from the blender by mixing it manually for at least 60 s until visually homogenous. The pre-mix was then added to the mixed SNAC and magnesium stearate. The mixing step was finalized in the blender by mixing for 10 min at 25 rpm. The blend was roller compacted.

The granules and microcrystalline cellulose were added to a blending container in order of decreasing content and mixed for 5 minutes at 32 rpm. Extragranular magnesium stearate was mixed with the granule blend by manual mixing using volume-doubling followed by 30 s mixing in the Turbula mixer at 32 rpm. Tablets were prepared from this composition.

Tablet Composition E

Magnesium stearate for the granule fraction was passed through a 355 μm sieve. Magnesium stearate was manually mixed with SNAC in a stainless steel bowl in corresponding volumes. Two cycles of geometric dilution was applied by mixing for around 60 s until the blend was visually homogenous. The remaining quantity of SNAC was transferred to a blender and was pre-mixed for 2 min at 25 rpm. The SNAC and magnesium stearate pre-mix was added to the blender and mixing was performed for 20 min at 25 rpm. Semaglutide, microcrystalline cellulose and povidone were weighed into a stainless steel bowl in the order of decreasing amounts and the components were mixed manually until visually homogenous. A geometric dilution was then performed using the mixed SNAC and magnesium stearate from the blender by mixing it manually for at least 60 s until visually homogenous. The pre-mix was then added to the mixed SNAC and magnesium stearate. The mixing step was finalized in the blender by mixing for 10 min at 25 rpm. The blend was roller compacted.

Extragranular magnesium stearate was mixed with the granules by manual mixing using volume-doubling followed by 30 s mixing in the Turbula mixer at 32 rpm. Tablets were prepared from this composition.

Tablet Composition F

Magnesium stearate for granule fraction one was passed through a 355 µm sieve. Magnesium stearate was manually mixed with SNAC in a stainless steel bowl in corresponding volumes. Two cycles of geometric dilution was applied by mixing for around 60 s until the blend was visually homogenous. The remaining quantity of SNAC was transferred to a blender and was pre-mixed for 2 min at 25 rpm. The SNAC and magnesium stearate pre-mix was added to the blender and mixing was performed for 20 min at 25 rpm. Microcrystalline cellulose was geometrically diluted using the mixed SNAC and magnesium stearate from the blender by mixing it manually for at least 60 s until visually homogenous. The pre-mix was then added to the mixed SNAC and magnesium stearate. The mixing step was finalized by mixing in the blender for 10 min at 25 rpm. The blend was roller compacted.

Semaglutide, microcrystalline cellulose (Avicel PH 101, FMC Biopolymer) and povidone (Kollidon 90F, BASF) for granule fraction two were weighed directly into a stainless steel bowl in the order of decreasing amounts and mixed manually for at least 3 min until visually homogenous before transferring the pre-mix to a 500 mL Duma bottle. The Duma bottle was closed with a lid and tumbled manually in a Turbula-like movement for 1 min. The blend was roller compacted.

The two types of granules were added to a blending container in order of decreasing content and mixed for 5 minutes at 32 rpm. Extragranular magnesium stearate was mixed with the granule blend by manual mixing using volume-doubling followed by 30 s mixing in the Turbula mixer at 32 rpm. Tablets were prepared from this composition.

Tablet Composition G

Magnesium stearate for the first granule fraction was passed through a 355 µm sieve. Magnesium stearate was manually mixed with SNAC in a plastic bag in corresponding volumes. Two cycles of geometric dilution was applied by mixing for around 60 s. The SNAC and magnesium stearate pre-mix was added to the blender followed by the addition of the remaining SNAC and mixing was performed for 50 min at 25 rpm. The blend was roller compacted. The granules were sieved through a 1000 and 90 µm mesh.

Compound A, microcrystalline cellulose and povidone for the second granule fraction were weighed directly into a stainless steel bowl in the order of decreasing amounts and mixed manually for at least 3 min until visually homogenous before transferring the pre-mix to a 500 mL Duma bottle. The Duma bottle was closed with a lid and tumbled manually in a Turbula-like movement for 3 min. The blend was roller compacted.

The two types of granules were added to a blending container and mixed for 20 minutes at 25 rpm. Extragranular magnesium stearate was passed through a 355 µm sieve and mixed with the granule blend by manual mixing using volume-doubling followed by 2 min mixing in the Turbula mixer at 25 rpm. Tablets were prepared from this composition.

Tablet Composition H

Magnesium stearate for granule fraction one was passed through a 355 µm sieve. Magnesium stearate was manually mixed with SNAC in a plastic bag in corresponding volumes. Two cycles of geometric dilution was applied by mixing for around 60 s. The SNAC and magnesium stearate pre-mix was added to the blender followed by the addition of the remaining SNAC and mixing was performed for 50 min at 25 rpm. Microcrystalline cellulose was then added to the mixed SNAC and magnesium stearate and the mixing step was finalized by mixing in the blender for 20 min at 25 rpm. The blend was roller compacted.

Compound A, microcrystalline cellulose (Avicel PH 101, FMC Biopolymer) and povidone (Kollidon 90F, BASF) for granule fraction two were weighed directly into a stainless steel bowl in the order of decreasing amounts and mixed manually for at least 3 min until visually homogenous before transferring the pre-mix to a 500 mL Duma bottle. The Duma bottle was closed with a lid and tumbled manually in a Turbula-like movement for at least 3 min. The blend was roller compacted.

The two types of granules were added to a blending container and mixed for 20 minutes at 25 rpm. Extragranular magnesium stearate was passed through a 355 µm sieve and mixed with the granule blend by manual mixing using volume-doubling followed by 2 minutes mixing in the Turbula mixer at 25 rpm. Tablets were prepared from this composition.

Example 2

Dissolution of GLP-1 and SNAC from Tablet Composition B

The dissolution of semaglutide and SNAC from tablet composition B was determined using Assay (I) described herein. The results are shown in Table 4. Corrected results are adjusted for the content of semaglutide or SNAC determined by analysis using Assay (III) described herein. The corrected results show that SNAC is released faster than semaglutide during the initial 20 min of dissolution. Furthermore, it shows that the difference between the faster release of SNAC compared to semaglutide is the largest in the dissolution medium with the pH-value of 2.5. Lastly, the data shows that in dissolution media with pH-values of 1.0 and 2.5 the amount of dissolved SNAC peaks within the initial 45 and 30 min, respectively.

TABLE 4

Dissolution of semaglutide and SNAC from tablet composition B

| | pH of dissolution media | | | | | | | | | | | |
|---|---|---|---|---|---|---|---|---|---|---|---|---|
| | 1.0 | | | | 2.5 | | | | 6.8 | | | |
| Dissolution time (min) | Semaglutide released (% of total) | | SNAC released (% of total) | | Semaglutide released (% of total) | | SNAC released (% of total) | | Semaglutide released (% of total) | | SNAC released (% of total) | |
| 0 | 0 | 0 | 0 | 0 | 0 | 0 | 0 | 0 | 0 | 0 | 0 | 0 |
| 5 | — | — | — | — | 8 | 9 | 19 | 19 | — | — | — | — |
| 10 | 9 | 10 | 13 | 13 | 17 | 18 | 28 | 28 | — | — | — | — |
| 15 | — | — | — | — | 22 | 24 | 32 | 32 | 45 | 49 | 53 | 52 |
| 20 | 17 | 18 | 19 | 19 | 27 | 29 | 34 | 34 | — | — | — | — |
| 30 | 20 | 22 | 20 | 20 | 35 | 38 | 33 | 33 | 74 | 81 | 81 | 80 |
| 45 | 23 | 25 | 20 | 20 | 42 | 46 | 30 | 30 | 86 | 94 | 92 | 91 |
| 60 | 24 | 26 | 19 | 19 | 46 | 50 | 28 | 28 | 92 | 100 | 96 | 95 |
| Corrected for actual content | Yes | No | Yes | No | Yes | No | Yes | No | Yes | No | Yes | No |

Example 3

Dissolution of GLP-1 and SNAC from Tablet Composition C

The dissolution of semaglutide and SNAC from tablet composition C was determined using Assay (I) described herein. The results are shown in Table 5. The results show that SNAC is released slower than semaglutide after the initial 5 min of dissolution in the dissolution media with low pH-values of 1.0 and 2.5. Corrected results are adjusted for the content of semaglutide or SNAC determined by analysis using Assay (III) described herein. During the initial 5 min of corrected dissolution in the dissolution medium with the pH-value of 2.5 SNAC is released equally fast as semaglutide. Furthermore, the corrected dissolution values show that SNAC is released faster than semaglutide in the dissolution medium with the pH-value of 6.8.

Example 4

Dissolution of GLP-1 and SNAC from Tablet Composition D

The dissolution of semaglutide and SNAC from tablet composition D was determined using Assay (I) described herein. The results are shown in Table 6. The results show that SNAC is released slower than semaglutide after the initial 5 min of dissolution in the dissolution media with low pH-values of 1.0 and 2.5. Corrected results are adjusted for the content of semaglutide or SNAC determined by analysis using Assay (III) described herein. During the initial 5 min of corrected dissolution in the dissolution medium with the pH-value of 2.5 SNAC is released equally fast with semaglutide. Furthermore, the corrected dissolution values show that SNAC is released faster than semaglutide in the dissolution medium with the pH-value of 6.8.

TABLE 5

Dissolution of semaglutide and SNAC from tablet composition C

| | pH of dissolution media | | | | | | | | | | | |
|---|---|---|---|---|---|---|---|---|---|---|---|---|
| | 1.0 | | | | 2.5 | | | | 6.8 | | | |
| Dissolution time (min) | Semaglutide released (% of total) | | SNAC released (% of total) | | Semaglutide released (% of total) | | SNAC released (% of total) | | Semaglutide released (% of total) | | SNAC released (% of total) | |
| 0 | 0 | 0 | 0 | 0 | 0 | 0 | 0 | 0 | 0 | 0 | 0 | 0 |
| 5 | — | — | — | — | 11 | 12 | 11 | 11 | — | — | — | — |
| 10 | 14 | 16 | 11 | 11 | 20 | 22 | 19 | 19 | — | — | — | — |
| 15 | — | — | — | — | 24 | 27 | 23 | 23 | 45 | 50 | 48 | 47 |
| 20 | 23 | 25 | 16 | 16 | 28 | 31 | 25 | 25 | — | — | — | — |
| 30 | 27 | 30 | 18 | 18 | 34 | 38 | 28 | 28 | 77 | 85 | 80 | 79 |
| 45 | 30 | 33 | 19 | 19 | 41 | 46 | 29 | 29 | 88 | 98 | 93 | 91 |
| 60 | 31 | 34 | 18 | 18 | 46 | 51 | 27 | 27 | 94 | 104 | 99 | 97 |
| Corrected for actual content | Yes | No | Yes | No | Yes | No | Yes | No | Yes | No | Yes | No |

TABLE 6

Dissolution of semaglutide and SNAC from tablet composition D

| | pH of dissolution media | | | | | | | | | | | |
|---|---|---|---|---|---|---|---|---|---|---|---|---|
| | 1.0 | | | | 2.5 | | | | 6.8 | | | |
| Dissolution time (min) | Semaglutide released (% of total) | | SNAC released (% of total) | | Semaglutide released (% of total) | | SNAC released (% of total) | | Semaglutide released (% of total) | | SNAC released (% of total) | |
| 0 | 0 | 0 | 0 | 0 | 0 | 0 | 0 | 0 | 0 | 0 | 0 | 0 |
| 5 | — | — | — | — | 11 | 12 | 11 | 11 | — | — | — | — |
| 10 | 10 | 11 | 8 | 8 | 17 | 19 | 16 | 16 | — | — | — | — |
| 15 | — | — | — | — | 21 | 23 | 19 | 19 | 33 | 37 | 35 | 35 |
| 20 | 17 | 19 | 12 | 12 | 23 | 26 | 20 | 20 | — | — | — | — |
| 30 | 23 | 26 | 15 | 15 | 28 | 31 | 22 | 22 | 59 | 66 | 62 | 62 |
| 45 | 26 | 29 | 16 | 16 | 33 | 37 | 24 | 24 | 75 | 83 | 77 | 77 |
| 60 | 27 | 30 | 15 | 15 | 38 | 42 | 25 | 25 | 82 | 91 | 84 | 84 |
| Corrected for actual content | Yes | No | Yes | No | Yes | No | Yes | No | Yes | No | Yes | No |

Example 5

Dissolution of GLP-1 and SNAC from Tablet Composition E

The dissolution of semaglutide and SNAC from tablet composition E was determined using Assay (I) described herein. The results are shown in Table 7. Corrected results are adjusted for the content of semaglutide or SNAC determined by analysis using Assay (III) described herein. The results show that SNAC is released slower than semaglutide during the entire dissolution time in a dissolution medium with a pH-value of 1.0. In a dissolution media with a pH-value of 2.5 the results show that SNAC initially is released faster than semaglutide during the initial 10 to 15 min of dissolution before becoming slower. Furthermore, the data shows that in dissolution medium with a pH-value of 2.5 the amount of dissolved SNAC peaks within the initial 20 min. Lastly, the corrected dissolution values show that SNAC is released faster than semaglutide in the dissolution medium with the pH-value of 6.8.

Example 6

Dissolution of GLP-1 and SNAC from Tablet Composition F

The dissolution of semaglutide and SNAC from tablet composition F was determined using Assay (I) described herein. The results are shown in Table 8. Corrected results are adjusted for the content of semaglutide or SNAC determined by analysis using Assay (III) described herein. The corrected results show that SNAC is released faster than semaglutide during the initial 20 to 30 min of dissolution. Furthermore, it shows that the difference between the faster release of SNAC compared to semaglutide is the largest in the dissolution medium with the pH-value of 2.5. Lastly, the data shows that in a dissolution medium with a pH-value of 2.5 the amount of dissolved SNAC peaks within the initial 30 min.

TABLE 7

Dissolution of semaglutide and SNAC from tablet composition E

| | pH of dissolution media | | | | | | | | | | | |
|---|---|---|---|---|---|---|---|---|---|---|---|---|
| | 1.0 | | | | 2.5 | | | | 6.8 | | | |
| Dissolution time (min) | Semaglutide released (% of total) | | SNAC released (% of total) | | Semaglutide released (% of total) | | SNAC released (% of total) | | Semaglutide released (% of total) | | SNAC released (% of total) | |
| 0 | 0 | 0 | 0 | 0 | 0 | 0 | 0 | 0 | 0 | 0 | 0 | 0 |
| 5 | — | — | — | — | 21 | 23 | 22 | 22 | — | — | — | — |
| 10 | 15 | 17 | 12 | 12 | 38 | 42 | 40 | 40 | — | — | — | — |
| 15 | — | — | — | — | 50 | 56 | 46 | 46 | 47 | 53 | 51 | 51 |
| 20 | 23 | 26 | 16 | 16 | 57 | 64 | 43 | 43 | — | — | — | — |
| 30 | 28 | 31 | 16 | 16 | 63 | 71 | 37 | 37 | 76 | 85 | 79 | 79 |
| 45 | 32 | 36 | 17 | 17 | 68 | 76 | 31 | 31 | 86 | 96 | 89 | 89 |
| 60 | 36 | 40 | 17 | 17 | 70 | 78 | 28 | 28 | 90 | 101 | 93 | 93 |
| Corrected for actual content | Yes | No | Yes | No | Yes | No | Yes | No | Yes | No | Yes | No |

TABLE 8

Dissolution of semaglutide and SNAC from tablet composition F

| Dissolution time (min) | pH 1.0 Semaglutide released (% of total) | pH 1.0 SNAC released (% of total) | pH 2.5 Semaglutide released (% of total) | pH 2.5 SNAC released (% of total) | pH 6.8 Semaglutide released (% of total) | pH 6.8 SNAC released (% of total) |
|---|---|---|---|---|---|---|
| 0 | 0 0 | 0 0 | 0 0 | 0 0 | 0 0 | 0 0 |
| 5 | — — | — — | 9 10 | 17 17 | — — | — — |
| 10 | 8 9 | 10 10 | 20 22 | 31 31 | — — | — — |
| 15 | — — | — — | 28 31 | 40 40 | 51 56 | 56 56 |
| 20 | 12 13 | 13 13 | 33 36 | 43 43 | — — | — — |
| 30 | 15 17 | 15 15 | 38 42 | 42 42 | 75 82 | 79 79 |
| 45 | 19 21 | 16 16 | 43 47 | 39 39 | 85 93 | 88 88 |
| 60 | 21 23 | 16 16 | 48 53 | 38 38 | 89 98 | 93 93 |
| Corrected for actual content | Yes No | Yes No | Yes No | Yes No | Yes No | Yes No |

Example 7

Bioavailability of GLP-1 in Dogs from Tablet Compositions B-F

Bioavailability of GLP-1 from tablet compositions B-F was determined in dogs according to Assay (II) described herein. The results are shown in Table 9.

TABLE 9

Bioavailability of GLP-1 in dogs from tablet compositions B-F

| Tablet composition | Bioavailability of GLP-1 in dogs (% F) |
|---|---|
| B | 0.7 |
| C | 0.5 |
| D | 0.3 |
| E | 0.4 |
| F | 1.0 |

The results show that tablet composition F provided a bioavailability of 1.0%. The results show that tablet composition B provided a bioavailability of 0.7%. The results show that tablet composition C provided a bioavailability of 0.5%. The results show that tablet composition E provided a bioavailability of 0.4%. The results show that tablet composition D provided a bioavailability of 0.3%.

Example 8

Dissolution of GLP-1 and SNAC from Tablet Composition G

The dissolution of Compound A and SNAC from tablet composition G was determined using Assay (I) described herein. The results are shown in Table 10. The results show that SNAC is released faster than Compound A during the initial 20 min of dissolution. Furthermore, it shows that the difference between the faster release of SNAC compared to Compound A is the largest in the dissolution medium with the pH-value of 2.5. Lastly, the data shows that in dissolution media with pH-value of 2.5 the amount of dissolved SNAC peaks within the initial 45 min, respectively.

TABLE 10

Dissolution of Compound A and SNAC from tablet composition G

| Dissolution time (min) | pH 2.5 Compound A released (% of total) | pH 2.5 SNAC released (% of total) | pH 6.8 Compound A released (% of total) | pH 6.8 SNAC released (% of total) |
|---|---|---|---|---|
| 0 | 0 | 0 | 0 | 0 |
| 5 | 9 | 17 | — | — |
| 10 | 16 | 24 | — | — |
| 15 | 21 | 26 | 38 | 49 |
| 20 | 25 | 28 | — | — |
| 30 | 32 | 28 | 70 | 79 |
| 45 | 39 | 28 | 85 | 92 |
| 60 | 43 | 26 | 91 | 96 |
| 120 | — | — | 95 | 101 |

Example 9

Dissolution of GLP-1 and SNAC from Tablet Composition H

The dissolution of Compound A and SNAC from tablet composition H was determined using Assay (I) described herein. The results are shown in Table 11. The results show that SNAC is released faster than Compound A during the initial 20 min of dissolution. Furthermore, it shows that the difference between the faster release of SNAC compared to Compound A is the largest in the dissolution medium with the pH-value of 2.5. Lastly, the data shows that in a dissolution medium with a pH-value of 2.5 the amount of dissolved SNAC peaks within the initial 30 min.

TABLE 11

Dissolution of Compound A and SNAC from tablet composition H

| Dissolution time | pH of dissolution media | | | |
|---|---|---|---|---|
| | 2.5 | | 6.8 | |
| | Compound A released (% of total) | SNAC released (% of total) | Compound A released (% of total) | SNAC released (% of total) |
| 0 | 0 | 0 | 0 | 0 |
| 5 | 10 | 19 | — | — |
| 10 | 19 | 31 | — | — |
| 15 | 26 | 37 | 37 | 47 |
| 20 | 31 | 38 | — | — |
| 30 | 36 | 34 | 63 | 75 |
| 45 | 42 | 29 | 74 | 83 |
| 60 | 46 | 27 | 79 | 87 |
| 120 | — | — | 89 | 97 |

Example 10

Bioavailability of GLP-1 in Dogs from Tablet Compositions G-H

Bioavailability of GLP-1 from tablet compositions G-H was determined in dogs according to Assay (II) described herein. The results are shown in Table 12.

TABLE 12

Bioavailability of GLP-1 in dogs from tablet compositions G-H

| Tablet composition | Bioavailability of GLP-1 in dogs (% F) |
|---|---|
| G | 2.1 |
| H | 2.5 |

The results show that tablet composition G provided a bioavailability of 2.1%. The results show that tablet composition H provided a bioavailability of 2.5%.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

---

---

The invention claimed is:

1. A solid dosage pharmaceutical composition comprising (1) a salt of N-(8-(2-hydroxybenzoyl)amino)caprylic acid (salt of NAC) and (2) a granule;
   wherein the granule comprises semaglutide, a binder, a filler, and no salt of NAC;
   wherein the filler is at least 15% (w/w) of the granule; and
   wherein the binder is less than 40% (w/w) of the granule.

2. The composition according to claim 1, wherein the salt of NAC is sodium N-(8-(2-hydroxybenzoyl)amino)caprylic acid (SNAC).

3. The composition according to claim 1, wherein the filler is microcrystalline cellulose.

4. The composition according to claim 1, wherein the filler is 50-75% (w/w) of the granule.

5. The composition according to claim 4, wherein the filler is microcrystalline cellulose.

6. The composition according to claim 1, wherein the binder is povidone.

7. The composition according to claim 1, wherein the binder is 15-25% (w/w) of the granule.

8. The composition according to claim 7, wherein the binder is povidone.

9. The composition according to claim 1, further comprising a lubricant that is not in the granule.

10. The composition according to claim 9, wherein the lubricant is magnesium stearate.

11. The composition according to claim 1, wherein the weight of the composition is in the range of 150 mg to 1000 mg.

12. The composition according to claim 11, wherein the weight of the composition is in the range of 300 mg to 600 mg.

13. The composition according to claim 12, wherein the weight of the composition is in the range of 350 mg to 450 g.

14. The composition according to claim 1, wherein the salt of NAC is sodium N-(8-(2-hydroxybenzoyl)amino) caprylic acid (SNAC), the filler is microcrystalline cellulose, and the binder is povidone.

15. The composition according to claim 1, wherein the filler is 50-75% (w/w) of the granule, and wherein the binder is 15-25% (w/w) of the granule.

16. The composition according to claim 15, wherein the salt of NAC is sodium N-(8-(2-hydroxybenzoyl)amino) caprylic acid (SNAC), the filler is microcrystalline cellulose, and the binder is povidone.

17. The composition according to claim 14, further comprising magnesium stearate that is not in the granule.

18. The composition according to claim 15, further comprising magnesium stearate that is not in the granule.

19. The composition according to claim 16, further comprising magnesium stearate that is not in the granule.

20. The composition according to claim 14, wherein the weight of the composition is in the range of 300 mg to 600 mg.

21. The composition according to claim 15, wherein the weight of the composition is in the range of 300 mg to 600 mg.

22. The composition according to claim 16, wherein the weight of the composition is in the range of 300 mg to 600 mg.

23. The composition according to claim 1, wherein the composition comprises at least 60% (w/w) of the salt of NAC.

24. The composition according to claim 23, wherein the salt of NAC is sodium N-(8-(2-hydroxybenzoyl)amino) caprylic acid (SNAC).

25. The composition according to claim 23, wherein the composition comprises at least 70% (w/w) of the salt of NAC.

26. The composition according to claim 25, wherein the salt of NAC is sodium N-(8-(2-hydroxybenzoyl)amino) caprylic acid (SNAC).

27. The composition according to claim 16, wherein the composition comprises at least 60% (w/w) of the SNAC.

28. The composition according to claim 27, wherein the composition comprises at least 70% (w/w) of the SNAC.

* * * * *

SEQUENCE LISTING

```
<160> NUMBER OF SEQ ID NOS: 2

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 40
<212> TYPE: PRT
<213> ORGANISM: Heloderma suspectum

<400> SEQUENCE: 2

His Gly Glu Gly Thr Phe Ile Thr Ser Asp Leu Ser Lys Gln Met Glu
1               5                   10                  15

Glu Glu Ala Val Arg Leu Phe Ile Glu Trp Leu Lys Asn Gly Gly Pro
            20                  25                  30

Ser Ser Gly Ala Pro Pro Pro Ser
            35                  40
```